(12) United States Patent
Sutcliffe et al.

(10) Patent No.: US 6,596,484 B1
(45) Date of Patent: *Jul. 22, 2003

(54) METHOD FOR SIMULTANEOUS SEQUENCE-SPECIFIC IDENTIFICATION AND DISPLAY OF MRNA'S

(75) Inventors: J. Gregor Sutcliffe, Cardiff, CA (US); Mark G. Erlander, Encinitas, CA (US); Karl W. Hasel, Solana Beach, CA (US)

(73) Assignee: The Scripps Research Institute, La Jolla, CA (US)

(*) Notice: Subject to any disclaimer, the term of this patent is extended or adjusted under 35 U.S.C. 154(b) by 119 days.

This patent is subject to a terminal disclaimer.

(21) Appl. No.: 09/650,229

(22) Filed: Aug. 29, 2000

Related U.S. Application Data

(60) Continuation of application No. 09/108,100, filed on Jun. 30, 1998, now Pat. No. 6,110,680, which is a continuation-in-part of application No. 09/035,190, filed on Mar. 5, 1998, now Pat. No. 6,030,784, and a continuation-in-part of application No. 08/544,577, filed on Oct. 17, 1995, now Pat. No. 5,807,680, which is a division of application No. 08/152,482, filed on Nov. 12, 1993, now Pat. No. 5,459,037, said application No. 09/035,190, is a division of application No. 08/152,482.

(51) Int. Cl.[7] .......................... C12Q 1/68; G01N 33/48; C12P 19/34
(52) U.S. Cl. .......................... 435/6; 702/20; 435/91.1; 435/91.2; 435/69.1
(58) Field of Search .......................... 435/6, 91.1, 91.2, 435/69.1; 702/20

(56) References Cited

U.S. PATENT DOCUMENTS

| | | | | |
|---|---|---|---|---|
| 5,459,037 A | * | 10/1995 | Sutcliffe et al. | 435/6 |
| 5,807,680 A | * | 9/1998 | Sutcliffe et al. | 435/6 |
| 6,030,784 A | * | 2/2000 | Sutcliffe et al. | 435/6 |
| 6,096,503 A | * | 8/2000 | Sutcliffe et al. | 435/6 |
| 6,110,680 A | * | 8/2000 | Sutcliffe et al. | 435/6 |
| 6,309,834 B1 | * | 10/2001 | Sutcliffe et al. | 435/6 |

* cited by examiner

Primary Examiner—Marianne P. Allen
Assistant Examiner—C. Mahatan
(74) Attorney, Agent, or Firm—Thomas Fitting

(57) ABSTRACT

An improved method for the simultaneous sequence-specific identification of mRNAs in a mRNA population allows the visualization of nearly every mRNA expressed by a tissue as a distinct band on a gel whose intensity corresponds roughly to the concentration of the mRNA. In general, the method comprises the formation of cDNA using anchor primers to fix a 3'-endpoint, producing cloned inserts from the cDNA in a vector containing a bacteriophage-specific promoter for subsequent RNA synthesis, generating linearized fragments of the cloned inserts, preparing cRNA, transcribing cDNA from the cRNA using a set of primers, and performing PCR using a 3'-primer whose sequence is derived from the vector and a set of 5'-primers that is derived from the primers used for transcription of cDNA from cRNA. The method can identify changes in expression of mRNA associated with the administration of drugs or with physiological or pathological conditions.

37 Claims, 3 Drawing Sheets pBS SK+/DGT1 Multiple Cloning Site

```
     SacI                                   NotI                      SmaI             NarI
5'- GAG CTC CAC CGC GGT GTC ACG ACT ATC TGC GGC CGC ATG CCC GGG AAT GGC
3'- CTC GAG GTG GCG CCA CAG TGC TGA TAG ACG CCG GCG TAC GGG CCC TTA CCG
     XhoI           AatII              ClaI           XhoI         AatII  SmaI
5'- GCC TCG AGA CGT CTT TAT CGA TAC CGT CGA CCT CGA ACT CGA GAC GTC CCG
3'- CGG AGC TCT GCA GAA ATA GCT ATG GCA GCT GGA GCT TGA GCT CTG CAG GGC
     NarI  KpnI
5'- GGC GCC TAG GTA CC -3'
3'- CCG CGG ATC CAT GG -5'
```

FIG. 3A pBS SK+/DGT2 Multiple Cloning Site

```
     SacI                                   NotI                      SmaI             NarI
5'- GAG CTC GTT TTC CCA GTC ACG ACT ATC TGC GGC CGC ATG CCC GGG AAT GGC
3'- CTC GAG CAA AAG GGT CAG TGC TGA TAG ACG CCG GCG TAC GGG CCC TTA CCG
     XhoI          AatII              ClaI           XhoI         AatII  SmaI
5'- GCC TCG AGA CGT TAT CGA TTA GCC TGA CTG AAG ACT CGA GAC GTC CCG
3'- CGG AGC TCT GCA ATA GCT AAT CGG ACT GAC TTC TGA GCT CTG CAG GGC
     NarI  KpnI
5'- GGC GCC TAG GTA CC -3'
3'- CCG CGG ATC CAT GG -5'
```

FIG. 3B pBS SK+/DGT3 Multiple Cloning Site

```
     SacI                                   NotI                      SmaI             NarI
5'- GAG CTC GTT TTC CCA GTC ACG ACT ATC TGC GGC CGC ATG CCC GGG AAT GGC
3'- CTC GAG CAA AAG GGT CAG TGC TGA TAG ACG CCG GCG TAC GGG CCC TTA CCG
     XhoI          AatII              ClaI           XhoI         AatII  SmaI
5'- GCC TCG AGA CGT CTA TAT CGA TTA GCC TGA CTG AAG ACT CGA GAC GTC CCG
3'- CGG AGC TCT GCA GAT ATA GCT AAT CGG ACT GAC TTC TGA GCT CTG CAG GGC
     NarI  KpnI
5'- GGC GCC TAG GTA CC -3'
3'- CCG CGG ATC CAT GG -5'
```

FIG. 3C

SEQUENCE LISTING

<160> NUMBER OF SEQ ID NOS: 27

<210> SEQ ID NO 1
<211> LENGTH: 14
<212> TYPE: DNA
<213> ORGANISM: Artificial Sequence
<220> FEATURE:
<221> NAME/KEY: misc_feature
<222> LOCATION: (1)..(14)
<223> OTHER INFORMATION: Synthetic primer

<400> SEQUENCE: 1
aactggaaga attc                                                      14

<210> SEQ ID NO 2
<211> LENGTH: 47
<212> TYPE: DNA
<213> ORGANISM: Artificial Sequence
<220> FEATURE:
<221> NAME/KEY: misc_feature
<222> LOCATION: (1)..(47)
<223> OTHER INFORMATION: Synthetic primer
<221> NAME/KEY: misc_feature
<222> LOCATION: (47)
<223> OTHER INFORMATION: N=A, C, G, or T

<400> SEQUENCE: 2
aactggaaga attcgcggcc gcaggaattt tttttttttt tttttvn                  47

<210> SEQ ID NO 3
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer
<221> NAME/KEY: misc_feature
<222> LOCATION: (17)..(18)
<223> OTHER INFORMATION: N= A, C, G or T

<400> SEQUENCE: 3
aggtcgacgg tatcggnn                                                  18

<210> SEQ ID NO 4
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 4
gaacaaaagc tggagctcca ccgc                                           24

<210> SEQ ID NO 5
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer
<221> NAME/KEY: misc_feature
<222> LOCATION: (17)..(19)
<223> OTHER INFORMATION: N= A, C, G or T

```
<400> SEQUENCE: 5
aggtcgacgg tatcggnnn                                              19

<210> SEQ ID NO 6
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
<222> LOCATION: (17)..(20)
<223> OTHER INFORMATION: N= A, C, G or T

<400> SEQUENCE: 6
aggtcgacgg tatcggnnnn                                             20

<210> SEQ ID NO 7
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer
<221> NAME/KEY: misc_feature
<222> LOCATION: (15)..(16)
<223> OTHER INFORMATION: N= A, C, G or T

<400> SEQUENCE: 7
gtcgacggta tcggnn                                                 16

<210> SEQ ID NO 8
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer

<400> SEQUENCE: 8
aagctggagc tccacc                                                 16

<210> SEQ ID NO 9
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer
<221> NAME/KEY: misc_feature
<222> LOCATION: (16)
<223> OTHER INFORMATION: N= A, C, G or T

<400> SEQUENCE: 9
ggtcgacggt atcggn                                                 16

<210> SEQ ID NO 10
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
```

```
<222> LOCATION: (20)
<223> OTHER INFORMATION: N= A, C, G or T

<400> SEQUENCE: 10
cttcagtcag gctaatcggn                                          20

<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
<222> LOCATION: (19)..(20)
<223> OTHER INFORMATION: N= A, C, G or T

<400> SEQUENCE: 11
ttcagtcagg ctaatcggnn                                          20

<210> SEQ ID NO 12
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
<222> LOCATION: (18)..(20)
<223> OTHER INFORMATION: N= A, C, G or T

<400> SEQUENCE: 12
tcagtcaggc taatcggnnn                                          20

<210> SEQ ID NO 13
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer
<221> NAME/KEY: misc_feature
<222> LOCATION: (14)..(16)
<223> OTHER INFORMATION: N= A, C, G or T

<400> SEQUENCE: 13
tcgacggtat cggnnn                                              16

<210> SEQ ID NO 14
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer
<221> NAME/KEY: misc_feature
<222> LOCATION: (13)..(16)
<223> OTHER INFORMATION: N= A, C, G or T

<400> SEQUENCE: 14
cgacggtatc ggnnnn                                              16

<210> SEQ ID NO 15
<211> LENGTH: 16
<212> TYPE: DNA
```

```
<213> ORGANISM: Artificial Sequence
<220> FEATURE:
<221> NAME/KEY: misc_feature
<222> LOCATION: (1)..(16)
<223> OTHER INFORMATION: Synthetic primer
<221> NAME/KEY: misc_feature
<222> LOCATION: (12)..(16)
<223> OTHER INFORMATION: N= A, C, G or T

<400> SEQUENCE: 15
gacggtatcg gnnnnn                                                      16

<210> SEQ ID NO 16
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer
<221> NAME/KEY: misc_feature
<222> LOCATION: (11)..(16)
<223> OTHER INFORMATION: N= A, C, G or T

<400> SEQUENCE: 16
acggtatcgg nnnnnn                                                      16

<210> SEQ ID NO 17
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
<222> LOCATION: (17)..(20)
<223> OTHER INFORMATION: N= A, C, G or T

<400> SEQUENCE: 17
cagtcaggct aatcggnnnn                                                  20

<210> SEQ ID NO 18
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Synthetic primer

<400> SEQUENCE: 18
gagctccacc gcggt                                                       15

<210> SEQ ID NO 19
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: Synthetic primer

<400> SEQUENCE: 19
gagctcgttt tcccag                                                      16

<210> SEQ ID NO 20
<211> LENGTH: 116
<212> TYPE: DNA
```

```
<213> ORGANISM: Artificial Sequence
<220> FEATURE:
<221> NAME/KEY: misc_feature
<222> LOCATION: (1)..(116)
<223> OTHER INFORMATION: Synthetic

<400> SEQUENCE: 20
gagctccacc gcggtgtcac gactatctgc ggccgcatgc ccgggaatgg cgcctcgaga      60
cgtctttatc gataccgtcg acctcgaact cgagacgtcc cgggcgccta ggtacc        116

<210> SEQ ID NO 21
<211> LENGTH: 113
<212> TYPE: DNA
<213> ORGANISM: Artificial Sequence
<220> FEATURE:
<221> NAME/KEY: misc_feature
<222> LOCATION: (1)..(113)
<223> OTHER INFORMATION: Synthetic

<400> SEQUENCE: 21
gagctcgttt tcccagtcac gactatctgc ggccgcatgc ccgggaatgg cgcctcgaga      60
cgttatcgat tagcctgact gaagactcga gacgtcccgg gcgcctaggt acc           113

<210> SEQ ID NO 22
<211> LENGTH: 113
<212> TYPE: DNA
<213> ORGANISM: Artificial Sequence
<220> FEATURE:
<221> NAME/KEY: misc_feature
<222> LOCATION: (1)..(113)
<223> OTHER INFORMATION: Synthetic

<400> SEQUENCE: 22
gagctcgttt tcccagtcac gactatctgc ggccgcatgc ccgggaatgg cgcctcgaga      60
cgtctatatc gattagcctg actgaagact cgagacgtcc cgggctaggt acc           113

<210> SEQ ID NO 23
<211> LENGTH: 46
<212> TYPE: DNA
<213> ORGANISM: Artificial Sequence
<220> FEATURE:
<221> NAME/KEY: misc_feature
<222> LOCATION: (1)..(46)
<223> OTHER INFORMATION: Synthetic primer

<400> SEQUENCE: 23
aactggaaga attcgcggcc gcaggaattt tttttttttt tttttv                    46

<210> SEQ ID NO 24
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer
<221> NAME/KEY: misc_feature
<222> LOCATION: (17)..(21)
<223> OTHER INFORMATION: N= A, C, G or t

<400> SEQUENCE: 24
aggtcgacgg tatcggnnnn n                                               21

<210> SEQ ID NO 25
<211> LENGTH: 22
<212> TYPE: DNA
```

```
<213> ORGANISM: Artificial Sequence
<220> FEATURE:
<221> NAME/KEY: misc_feature
<222> LOCATION: (1)..(22)
<223> OTHER INFORMATION: Synthetic primer
<221> NAME/KEY: misc_feature
<222> LOCATION: (17)..(22)
<223> OTHER INFORMATION: N= A, C, G or T

<400> SEQUENCE: 25
aggtcgacgg tatcggnnnn nn                                              22

<210> SEQ ID NO 26
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
<222> LOCATION: (16)..(20)
<223> OTHER INFORMATION: N= A, C, G or T

<400> SEQUENCE: 26
agtcaggcta atcggnnnnn                                                 20

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
<221> NAME/KEY: misc_feature
<222> LOCATION: (15)..(20)
<223> OTHER INFORMATION: N= A, C, G or T

<400> SEQUENCE: 27
gtcaggctaa tcggnnnnnn                                                 20
```

METHOD FOR SIMULTANEOUS SEQUENCE-SPECIFIC IDENTIFICATION AND DISPLAY OF MRNA'S

CROSS REFERENCE TO RELATED APPLICATIONS

The present application is a continuation of U.S. application Ser. No. 09/108,100, filed Jun. 30, 1998, now U.S. Pat. No. 6,110,680, which is a continuation-in-part of U.S. application Ser. No. 09/035,190, filed Mar. 5, 1998, which issued as U.S. Pat. No. 6,030,784 on Feb. 29, 2000, and U.S. application Ser. No. 08/544,577, filed Oct. 17, 1995, which issued as U.S. Pat. No. 5,807,680 on Sep. 15, 1998, which are both divisional applications of U.S. patent application Ser. No. 08/152,482 filed Nov. 12, 1993, which issued as U.S. Pat. No. 5,459, 037 on Oct. 17, 1995, the teachings of which are incorporated by reference.

GOVERNMENT RIGHTS

The research underlying this invention has been funded by the National Institutes of Health, Grant No. NS22347/GM32355. The government may have certain rights in this invention.

BACKGROUND OF THE INVENTION

This invention is directed to methods for simultaneous identification of differentially expressed mRNAs, as well as measurements of their relative concentrations.

An ultimate goal of biochemical research ought to be a complete characterization of the protein molecules that make up an organism. This would include their identification, sequence determination, demonstration of their anatomical sites of expression, elucidation of their biochemical activities, and understanding of how these activities determine organismic physiology. For medical applications, the description should also include information about how the concentration of each protein changes in response to pharmaceutical or toxic agents.

Let us consider the scope of the problem: How many genes are there? The issue of how many genes are expressed in a mammal is still unsettled after at least two decades of study. There are few direct studies that address patterns of gene expression in different tissues. Mutational load studies (J. O. Bishop, "The Gene Numbers Game," Cell 2:81–86 (1974); T. Ohta & M. Kimura, "Functional Organization of Genetic Material as a Product of Molecular Evolution," Nature 223:118–119 (1971)) have suggested that there are between $3 \times 10^4$ and $10^5$ essential genes.

Before cDNA cloning techniques, information on gene expression came from RNA complexity studies: analog measurements (measurements in bulk) based on observations of mixed populations of RNA molecules with different specificities in abundances. To an unexpected extent, early analog complexity studies were distorted by hidden complications of the fact that the molecules in each tissue that make up most of its mRNA mass comprise only a small fraction of its total complexity. Later, cDNA cloning allowed digital measurements (i.e., sequence-specific measurements on individual species) to be made; hence, more recent concepts about mRNA expression are based upon actual observations of individual RNA species.

Brain, liver, and kidney are the mammalian tissues that have been most extensively studied by analog RNA complexity measurements. The lowest estimates of complexity are those of Hastie and Bishop (N. D. Hastie & J. B. Bishop, "The Expression of Three Abundance Classes of Messenger RNA in Mouse Tissues," Cell 9:761–774 (1976)), who suggested that $26 \times 10^6$ nucleotides of the $3 \times 10^9$ base pair rodent genome were expressed in brain, $23 \times 10^6$ in liver, and $22 \times 10^6$ in kidney, with nearly complete overlap in RNA sets. This indicates a very minimal number of tissue-specific mRNAs. However, experience has shown that these values must clearly be underestimates, because many mRNA molecules, which were probably of abundances below the detection limits of this early study, have been shown to be expressed in brain but detectable in neither liver nor kidney. Many other researchers (J. A. Bantle & W. E. Hahn, "Complexity and Characterization of Polyadenylated RNA in the Mouse Brain," Cell 8:139–150 (1976); D. M. Chikaraishi, "Complexity of Cytoplasmic Polyadenylated and Non-Adenylated Rat Brain Ribonucleic Acids," Biochemistry 18:3249–3256 (1979)) have measured analog complexities of between $100-200 \times 10^6$ nucleotides in brain, and 2-to-3-fold lower estimates in liver and kidney. Of the brain mRNAs, 50–65% are detected in neither liver nor kidney. These values have been supported by digital cloning studies (R. J. Milner & J. G. Sutcliffe, "Gene Expression in Rat Brain," Nucl. Acids Res. 11:5497–5520 (1983)).

Analog measurements on bulk mRNA suggested that the average mRNA length was between 1400–1900 nucleotides. In a systematic digital analysis of brain mRNA length using 200 randomly selected brain cDNAs to measure RNA size by northern blotting (Milner & Sutcliffe, supra), it was found that, when the mRNA size data were weighted for RNA prevalence, the average length was 1790 nucleotides, the same as that determined by analog measurements. However, the mRNAs that made up most of the brain mRNA complexity had an average length of 5000 nucleotides. Not only were the rarer brain RNAs longer, but they tended to be brain specific, while the more prevalent brain mRNAs were more ubiquitously expressed and were much shorter on average.

These concepts about mRNA lengths have been corroborated more recently from the length of brain mRNA whose sequences have been determined (J. G. Sutcliffe, "mRNA in the Mammalian Central Nervous System," Annu. Rev. Neurosci, 11:157–198 (1988)). Thus, the $1-2 \times 10^8$ nucleotide complexity and 5000-nucleotide average mRNA length calculates to an estimated 30,000 mRNAs expressed in the brain, of which about $\frac{2}{3}$ are not detected in liver or kidney. Brain apparently accounts for a considerable portion of the tissue-specific genes of mammals. Most brain mRNAs are expressed at low concentration. There are no total-mammal mRNA complexity measurements, nor is it yet known whether 5000 nucleotides is a good mRNA-length estimate for non-neural tissues. A reasonable estimate of total gene number might be between 50,000 and 100,000.

What is most needed to advance by a chemical understanding of physiological function is a menu of protein sequences encoded by the genome plus the cell types in which each is expressed. At present, protein sequences can be reliably deduced only from cDNAs, not from genes, because of the presence of the intervening sequences (introns) in the genomic sequences. Even the complete nucleotide sequence of a mammalian genome will not substitute for characterization of its expressed sequences. Therefore, a systematic strategy for collecting transcribed sequences and demonstrating their sites of expression is needed. Such a strategy would be of particular use in determining sequences expressed differentially within the brain. It is necessarily an eventual goal of such a study to achieve closure; that is, to identify all mRNAs. Closure can be difficult to obtain due to the differing prevalence of various mRNAs and the large number of distinct mRNAs expressed by many distinct tissues. The effort to obtain it allows one to obtain a progressively more reliable description of the dimensions of gene space.

Studies carried out in the laboratory of Craig Venter (M. D. Adams et al., "Complementary DNA Sequencing: Expressed Sequence Tags and Human Genome Project," Science 252:1651–1656 (1991); M. D. Adams et al., "Sequence Identification of 2,375 Human Brain Genes," Nature 355:632–634 (1992)) have resulted in the isolation of randomly chosen cDNA clones of human brain mRNAs, the determination of short single-pass sequences of their 3'-ends, about 300 base pairs, and a compilation of some 2500 of these as a database of "expressed sequence tags." This database, while useful, fails to provide any knowledge of differential expression. It is therefore important to be able to recognize genes based on their overall pattern of expression within regions of brain and other tissues and in response to various paradigms, such as various physiological or pathological states or the effects of drug treatment, rather than simply their expression in a single tissue.

Other work has focused on the use of the polymerase chain reaction (PCR) to establish a database. Williams et al. (J. G. K. Williams et al.; "DNA Polymorphisms Amplified by Arbitrary Primers Are Useful as Genetic Markers," Nucl. Acids Res. 18:6531–6535 (1990)) and Welsh & McClelland (J. Welsh & McClelland, "Genomic Fingerprinting Using Arbitrarily Primed PCR and a Matrix of Pairwise Combinations of Primers," Nucl. Acids Res. 18:7213–7218 (1990)) showed that single 10-mer primers of arbitrarily chosen sequences, i.e., any 10-mer primer off the shelf, when used for PCR with complex DNA templates such as human, plant, yeast, or bacterial genomic DNA, gave rise to an array of PCR products. The priming events were demonstrated to involve incomplete complementarity between the primer and the template DNA. Presumably, partially mismatched primer-binding sites are randomly distributed through the genome. Occasionally, two of these sites in opposing orientation were located closely enough together to give rise to a PCR product band. There were on average 8–10 products, which varied in size from about 0.4 to about 4 kb and had different mobilities for each primer. The array of PCR products exhibited differences among individuals of the same species. These authors proposed that the single arbitrary primers could be used to produce restriction fragment length polymorphism (RFLP)-like information for genetic studies. Others have applied this technology (S. R. Woodward et al., "Random Sequence Oligonucleotide Primers Detect Polymorphic DNA Products Which Segregate in Inbred Strains of Mice," Mamm. Genome 3:73–78 (1992); J. H. Nadeau et al., "Multilocus Markers for Mouse Genome Analysis: PCR Amplification Based on Single Primers of Arbitrary Nucleotide Sequence," Mamm. Genome 3:55–64 (1992)).

Two groups (J. Welsh et al., "Arbitrarily Primed PCR Fingerprinting of RNA," Nucl. Acids Res. 20:4965–4970 (1992); P. Liang & A. B. Pardee, "Differential Display of Eukaryotic Messenger RNA by Means of the Polymerase Chain Reaction," Science 257:967–971 (1992)) adapted the method to compare mRNA populations. In the study of Liang and Pardee, this method, called mRNA differential display, was used to compare the population of mRNAs expressed by two related cell types, normal and tumorigenic mouse A31 cells. For each experiment, they used one arbitrary 10-mer as the 5'-primer and an oligonucleotide complementary to a subset of poly A tails as a 3' anchor primer, performing PCR amplification in the presence of $^{35}$S-dNTPs on cDNAs prepared from the two cell types. The products were resolved on sequencing gels and 50–100 bands ranging from 100–500 nucleotides were observed. The bands presumably resulted from amplification of cDNAs corresponding to the 3'-ends of mRNAs that contain the complement of the 3' anchor primer and a partially mismatched 5' primer site, as had been observed on genomic DNA templates. For each primer pair, the pattern of bands amplified from the two cDNAs was similar, with the intensities of about 80% of the bands being indistinguishable. Some of the bands were more intense in one or the other of the PCR samples; a few were detected in only one of the two samples.

Further studies (P. Liang et al., "Distribution and Cloning of Eukaryotic mRNAs by Means of Differential Display: Refinements and Optimization," Nucl. Acids Res. 21:3269–3275 (1993)) have demonstrated that the procedure works with low concentrations of input RNA (although it is not quantitative for rarer species), and the specificity resides primarily in the last nucleotide of the 3' anchor primer. At least a third of identified differentially detected PCR products correspond to differentially expressed RNAs, with a false positive rate of at least 25%.

If all of the 50,000 to 100,000 mRNAs of the mammal were accessible to this arbitrary-primer PCR approach, then about 80–95 5' arbitrary primers and 12 3' anchor primers would be required in about 1000 PCR panels and gels to give a likelihood, calculated by the Poisson distribution, that about two-thirds of these mRNAs would be identified.

It is unlikely that all mRNAs are amenable to detection by this method for the following reasons. For an mRNA to surface in such a survey, it must be prevalent enough to produce a signal on the autoradiograph and contain a sequence in its 3' 500 nucleotides capable of serving as a site for mismatched primer binding and priming. The more prevalent an individual mRNA species, the more likely it would be to generate a product. Thus, prevalent species may give bands with many different arbitrary primers. Because this latter property would contain an unpredictable element of chance based on selection of the arbitrary primers, it would be difficult to approach closure by the arbitrary primer method. Also, for the information to be portable from one laboratory to another and reliable, the mismatched priming must be highly reproducible under different laboratory conditions using different PCR machines, with the resulting slight variation in reaction conditions. As the basis for mismatched priming is poorly understood, this is a drawback of building a database from data obtained by the Liang & Pardee differential display method.

There is therefore a need for an improved method of differential display of mRNA species that reduces the uncertain aspect of 5'-end generation and allows data to be absolutely reproducible in different settings. Preferably, such a method does not depend on potentially irreproducible mismatched priming. Preferably, such a method reduces the number of PCR panels and gels required for a complete survey and allows double-strand sequence data to be rapidly accumulated. Preferably, such an improved method also reduces, if not eliminates, the number of concurrent signals obtained from the same species of mRNA.

SUMMARY

We have developed an improved method for the simultaneous sequence-specific identification of mRNAs in a mRNA population. In general, this method comprises:

(1) preparing double-stranded cDNAs from a mRNA population using a mixture of 12 anchor primers, the anchor primers each including: (i) a tract of from 7 to 40 T residues; (ii) a site for cleavage by a restriction endonuclease that recognizes more than six bases, the site for cleavage being located to the 5'-side of the tract of T residues; (iii) a first stuffer segment of from 4 to 40 nucleotides, the first stuffer segment being located to the 5'-side of the site for cleavage by the restriction endonuclease; and (iv) phasing residues -V-N located at the 3' end of each of the anchor primers, wherein V is a deoxyribonucleotide selected from the group consisting of A, C, and G; and N is a deoxyribonucleotide selected from the group consisting of A, C, G, and T, the mixture including anchor primers containing all possibilities for V and N;

(2) producing cloned inserts from a suitable host cell that has been transformed by a vector, the vector having the cDNA sample that has been cleaved with a first restriction endonuclease and a second restriction endonuclease inserted therein, the cleaved cDNA sample being inserted in the vector in an orientation that is antisense with respect to a bacteriophage-specific promoter within the vector, the first restriction endonuclease recognizing a four-nucleotide sequence and the second restriction endonuclease cleaving at a single site within each member of the mixture of anchor primers;

(3) generating linearized fragments of the cloned inserts by digestion with at least one restriction endonuclease that is different from the first and second restriction endonucleases;

(4) generating a cRNA preparation of antisense cRNA transcripts by incubation of the linearized fragments with a bacteriophage-specific RNA polymerase capable of initiating transcription from the bacteriophage-specific promoter;

(5) dividing the cRNA preparation into sixteen subpools and transcribing first-strand cDNA from each subpool, using a thermostable reverse transcriptase and one of sixteen 5'-RT primers whose 3'-terminus is -N-N, wherein N is one of the four deoxyribonucleotides A, C, G, or T, the 5'-RT primer being at least 15 nucleotides in length, corresponding in sequence to the 3'-end of the bacteriophage-specific promoter, and extending across into at least the first two nucleotides of the cRNA, the mixture including all possibilities for the 3'-terminal two nucleotides;

(6) using the product of transcription in each of the sixteen subpools as a template for a polymerase chain reaction with a 3'-PCR primer that corresponds in sequence to a sequence in the vector adjoining the site of insertion of the cDNA sample in the vector and a 5'-PCR primer selected from the group consisting of: (i) the 5'-RT primer from which first-strand cDNA was made for that subpool; (ii) the 5'-RT primer from which the first-strand cDNA was made for that subpool extended at its 3'-terminus by an additional residue -N, where N can be any of A, C, G, or T; and (iii) the 5'-RT primer used for the synthesis of first-strand cDNA for that subpool extended at its 3'-terminus by two additional residues -N-N, wherein N can be any of A, C, G, or T, to produce polymerase chain reaction amplified fragments; and (7) resolving the polymerase chain reaction amplified fragments by electrophoresis to display bands representing the 3'-ends of mRNAs present in the sample.

In another preferred embodiment, the method comprises the steps of:

(a) preparing a double-stranded cDNA population from an mRNA population using a mixture of anchor primers, the anchor primers each including: (i) a tract of from 7 to 40 T residues; (ii) a site for cleavage by a first restriction endonuclease that recognizes more than six bases, the site for cleavage being located to the 5'-side of the tract of T residues; (iii) a first stuffer segment of from 4 to 40 nucleotides, the first stuffer segment being located to the 5'-side of the site for cleavage by the first restriction endonuclease; and (iv) phasing residues located at the 3' end of each of the anchor primers selected from the group consisting of -V, and -V-N , wherein V is a deoxyribonucleotide selected from the group consisting of A, C, and G; and N is a deoxyribonucleotide selected from the group consisting of A, C, G, and T, the mixture including anchor primers containing all possibilities for V and N where the phasing residues in the mixture are defined by one of -V, or -V-N;

(b) cleaving the double-stranded cDNA population with the first restriction endonuclease and with a second restriction endonuclease, the second restriction endonuclease recognizing a four-nucleotide sequence, to form a population of double-stranded cDNA molecules having first and second termini, respectively;

(c) inserting the double-stranded cDNA molecules from step (b) each into a vector in an orientation that is antisense with respect to a bacteriophage-specific promoter within the vector to form a population of vectors containing the inserted cDNA molecules, said inserting defining 3' and 5' flanking vector sequences such that 5' is upstream from the sense strand of the inserted cDNA and 3' is downstream of the sense strand, and said vector having a 3' flanking nucleotide sequence of from at least 15 nucleotides in length between said first restriction endonuclease site and a site defining transcription initiation in said promoter;

(d) generating linearized fragments containing the inserted cDNA molecules by digestion of the vectors produced in step (c) with at least one restriction endonuclease that does not recognize sequences in the inserted cDNA molecules or in the bacteriophage-specific promoter, but does recognize sequences in the vector such that the resulting linearized fragments have a 5' flanking vector sequence of at least 15 nucleotides 5' to the site of insertion of the cDNA sample into the vector at the cDNA's second terminus;

(e) generating a cRNA preparation of antisense cRNA transcripts by incubation of the linearized fragments with a bacteriophage-specific RNA polymerase capable of initiating transcription from the bacteriophage-specific promoter;

(f) dividing the cRNA preparation into subpools and transcribing first-strand cDNA from each subpool, using a reverse transcriptase and one of the 5'-RT primers defined as having a 3'-terminus consisting of -$N_x$, wherein "N" is one of the four deoxyribonucleotides A, C, G, or T, and "x" is an integer from 1 to 5, the 5'-RT primer being 15 to 30 nucleotides in length and complementary to the 5' flanking vector sequence with the 5'-RT primer's complementarity extending across into the insert-specific nucleotides of the cRNA in a number of nucleotides equal to "x", wherein a different one of said 5'-RT primers is used in different subpools and wherein there are 4 subpools if "x"=1, 16 subpools if "x"=2, 64 subpools if "x"=3, 256 subpools if "x"=4, and 1,024 subpools if "x"=5;

(g) using the product of first-strand cDNA transcription in each of the subpools as a template for a polymerase chain reaction with a 3'-PCR primer of 15 to 30 nucleotides in length that is complementary to 3' flanking vector sequences between said first restriction endonuclease site and the site defining transcription initiation by the bacteriophage-specific promoter and a 5'-PCR primer having a 3'-terminus consisting of $-N_x$-$N_y$, where "N" and "x" are as in step (f), $-N_x$ is the same sequence as in the 5'-RT primer from which first-strand cDNA was made for that subpool, and "y" is a whole integer such that x+y equals an integer selected from the group consisting of 3, 4, 5 and 6, the primer being 15 to 30 nucleotides in length and complementary to the 5' flanking vector sequence with the 5'-PCR primer's complementarity extending across into the insert-specific nucleotides of the cRNA in a number of nucleotides equal to "x+y", to produce polymerase chain reaction amplified fragments; and (h) resolving the polymerase chain reaction amplified fragments to generate a display of sequence-specific products representing the 3'-ends of different mRNAs present in the mRNA population.

Typically, the anchor primers each have 18 T residues in the tract of T residues, and the first stuffer segment of the anchor primers is 14 residues in length. A suitable sequence for the first stuffer segment is A-A-C-T-G-G-A-A-G-A-A-T-T-C (SEQ ID NO: 1). Typically, the site for cleavage by a first restriction endonuclease that recognizes more than six bases is the NotI cleavage site. Suitable anchor primers can also comprise a second stuffer segment interposed between the site for cleavage by a first restriction endonuclease that recognizes more than six bases and the tract of T residues. Phasing residues that are at the 3' end of the anchor primer and 3' to the tract of T residues are chosen from the group consisting of -V and -V-N, where V is a deoxyribonucleotide selected from the group consisting of A, C, and G; and N is a deoxyribonucleotide selected from the group consisting of A, C, G, and T.

In one preferred embodiment, the anchor primer has the sequence A-A-C-T-G-G-A-A-G-A-A-T-T-C-G-C-G-G-C-C-G-C-A-G-G-A-A-T-T-T-T-T-T-T-T-T-T-T-T-T-T-T-T-T-T-T-V-N (SEQ ID NO: 2), including a first stuffer segment of A-A-C-T-G-G-A-A-G-A-A-T-T-C that is 5' to the NotI site G-C-G-G-C-C-G-C, a second stuffer sequence A-G-G-A-A interposed between the restriction endonuclease cleavage site and the tract of T residues, and phasing residues -V-N. In other preferred embodiments, the phasing residues of the anchor primer used in step (a) are -V.

Typically the first restriction endonuclease that recognizes more than six bases is selected from the group consisting of AscI, BaeI, FseI, NotI, PacI, PmeI, PpuMI, RsrII, SapI, SexAI, SfiI, SgfI, SgrAI SrfI, Sse8387.I and SwaI. Typically the second restriction endonuclease recognizing a four-nucleotide sequence is selected from the group consisting of MboI, DpnII, Sau3AI, Tsp509I, HpaII, BfaI, Csp6I, MseI, HhaI, NlaIII, TaqI, MspI, MaeII and HinP1I.

Typically the value of "x" in step (f) is 1 or 2. Typically the value of "y" instep (g) is 3 or 4. In one embodiment, the phasing residues in step (a) are -V-N, the "x" in step (f) is 2, and the "y" in step (g) is 2. In another embodiment, the phasing residues in step (a) are -V-N, the "x" in step (f) is 1, and the "y" in step (g) is 3. In another embodiment, the phasing residues in step (a) are -V-N, the "x" in step (f) is 1, and the "y" in step (g) is 4.

Another embodiment, the phasing residues in step (a) are -V, the "x" in step (f) is 1, and the "y" in step (g) is 3. In a further embodiment, the phasing residues in step (a) are -V, the "x" in step (f) is 1, and the "y" in step (g) is 4.

Typically, the anchor primers each have 18 T residues in the tract of T residues, and the first stuffer segment of the anchor primers is 14 residues in length.

Suitable vectors are pBC SK⁺ and pBS SK⁺ (Stratagene). In another aspect, the invention provides improved vectors based on pBS SK⁺ that are designed for the practice of the invention such as pBS SK⁺/DGT1, pBS SK⁺/DGT2 and pBS SK⁺/DGT3, described in detail below. Such improved vectors can also be based on pBC SK⁺ or other suitable vectors well known to one skilled in the art.

Preferred vectors are improved vectors based on the plasmid vector pBluescript (pBS or pBC) SK+ (Stratagene) in which a portion of the nucleotide sequence from positions 656 to 764 was removed and replaced with a sequence of at least 110 nucleotides including a NotI restriction endonuclease site. This region, designated the multiple cloning site (MCS), spans the portion of the nucleotide sequence from the SacI site to the KpnI site.

The vector can be the plasmid pBC SK⁺ cleaved with ClaI and NotI, in which case the 3'-PCR primer in step (6) can be G-A-A-C-A-A-A-A-G-C-T-G-G-A-G-C-T-C-C-A-C-C-G-C (SEQ ID NO: 4). In preferred embodiment, the vector is chosen from the group consisting of pBC SK⁺, pBS SK⁺ and pBS SK⁺/DGT1 and the 3'-PCR primer in step (f) is G-A-G-C-T-C-C-A-C-C-G-C-G-G-T (SEQ ID NO: 18).

Typically the restriction endonuclease used in step (d) has a nucleotide sequence recognition that includes the four-nucleotide sequence of the second restriction endonuclease used in step (b). In general, the sites for such restriction endonucleases must be in the vector sequence 5' to the ClaI site as well as in the MCS between the ClaI site and the NotI site.

In one embodiment, vector is the plasmid pBC SK⁺ and MspI is used both as the second restriction endonuclease and as the linearization restriction endonuclease used in step (d).

In another embodiment, vector is the plasmid pBC SK⁺, the second restriction endonuclease is chosen from the group consisting of MspI, MaeII, TaqI and HinP1I and the linearization in step (d) is accomplished by a first digestion with SmaI followed by a second digestion with a mixture of KpnI and ApaI.

In other embodiments the vector is chosen from the group consisting of pBS SK⁺/DGT1, pBS SK⁺/DGT2 and pBS SK⁺/DGT3. In such embodiments, one suitable enzyme combination is provided where the second restriction endonuclease is MspI and the restriction endonuclease used in step (d) is SmaI. Another suitable combination is provided where the second restriction endonuclease is TaqI and the restriction endonuclease used in step (d) is XhoI. A further suitable combination is provided where the second restriction endonuclease is HinP1I and the restriction endonuclease used in step (d) is NarI. Yet another suitable combination is provided where the second restriction endonuclease is MaeII and the restriction endonuclease used in step (d) is AatII.

Typically the bacteriophage-specific promoter is selected from the group consisting of T3 promoter, T7 promoter and SP6 promoter. Most typically it is the T3 promoter.

Typically, the sixteen 5'-RT primers for priming of transcription of cDNA from cRNA have the sequence A-G-G-T-C-G-A-C-G-G-T-A-T-C-G-G-N-N (SEQ ID NO: 3). In another preferred embodiment, the four 5'-RT primers for priming of transcription of cDNA from cRNA have the sequence G-G-T-C-G-A-C-G-G-T-A-T-C-G-G-N (SEQ ID NO: 9).

The second restriction endonuclease recognizing a four-nucleotide sequence is typically MspI; alternatively, it can be TaqI, MaeII or HinP1I. The restriction endonuclease cleaving at a single site in each of the mixture of anchor primers is typically. NotI.

Typically, the mRNA population has been enriched for polyadenylated mRNA species.

A typical host cell is a strain of *Escherichia coli*.

The step of generating linearized fragments of the cloned inserts typically comprises:

(a) dividing the plasmid containing the insert into two fractions, a first fraction cleaved with the restriction endonuclease XhoI and a second fraction cleaved with the restriction endonuclease Sal I;

(b) recombining the first and second fractions after cleavage;

(c) dividing the recombined fractions into thirds and cleaving the first third with the restriction endonuclease HindIII, the second third with the restriction endonuclease BamHI, and the third third with the restriction endonuclease EcoRI; and (d) recombining the thirds after digestion in order to produce a population of linearized fragments of which about one-sixth of the population corresponds to the product of cleavage by each of the possible combinations of enzymes.

In another embodiment, wherein the vector is chosen from the group consisting of pBC SK+ and pBS SK+, and MspI is the second restriction endonuclease, MspI can be used as the linearization restriction endonuclease used in step (d). Alternatively, where the vector is the plasmid pBC SK+, linearization can be accomplished by a first digestion with SmaI followed by a second digestion with a mixture of KpnI and ApaI.

In other embodiments, the vector is chosen from the group consisting of pBS SK+/DGT1, pBS SK+/DGT2 and pBS SK+/DGT3 and the linearization restriction endonuclease used in step (d) is chosen from the group consisting of SmaI, XhoI, NarI and AatII.

Typically, the step of resolving the polymerase chain reaction amplified fragments by electrophoresis comprises electrophoresis of the fragments on at least two gels.

Each sequence-specific PCR product, or polymerase chain reaction amplified fragment, is identified by a digital address consisting of a sequence identifier, the length of the product in nucleotide residues and the intensity of labeling of the PCR product, defined as the area under the peak of the detector output for that PCR product.

The sequence identifier is defined by a 5' component and a 3' component. The 5' component of the sequence identifier is the recognition site of the second restriction nuclease used to cleave the double stranded cDNA population prepared from the original mRNA population. Typically, the restriction endonuclease is MspI, and the 5' component of the sequence identifier is -C-C-G-G. The 3' component of the sequence identifier is the sequence defined by the 3' terminus sequence of the 5'PCR primer. For example, the 3' component of the sequence identifier of the PCR product indicated as "111" in FIG. 2 is -C-T-G-C. Therefore, in this case, the sequence identifier would be -C-C-G-G-C-T-G-C.

Typically, a database comprising the digital address, as defined above as sequence identifier and the length of the sequence-specific PCR product in nucleotide residues and the intensity of labeling of the PCR product, defined as the area under the peak of the detector output for that PCR product, is constructed and maintained using suitable computer hardware and computer software. Preferably, such a database further comprises data concerning sequence relationships, gene mapping, cellular distributions, experimental treatment conditions and any other information considered relevant to gene function.

The method can further comprise determining the sequence of the 3'-end of at least one of the mRNAs, such as by:

(1) eluting at least one cDNA corresponding to a mRNA from an electropherogram in which bands representing the 3'-ends of mRNAs present in the sample are displayed;

(2) amplifying the eluted cDNA in a polymerase chain reaction;

(3) cloning the amplified cDNA into a plasmid;

(4) producing DNA corresponding to the cloned DNA from the plasmid; and (5) sequencing the cloned cDNA.

Another aspect of the invention is a method of simultaneous sequence-specific identification of mRNAs corresponding to members of an antisense cRNA pool representing the 3'-ends of a population of mRNAs, the antisense cRNAs that are members of the antisense cRNA pool being terminated at their 5'-end with a primer sequence corresponding to a bacteriophage-specific vector and at their 3'-end with a sequence corresponding in sequence to a sequence of the vector.

The method comprises;

(1) dividing the members of the antisense cRNA pool into sixteen subpools and transcribing first-strand cDNA from each subpool, using a thermostable reverse transcriptase and one of sixteen 5'-RT primers whose 3'-terminus is -N-N, wherein N is one of the four deoxyribonucleotides A, C, G, or T, the 5'-RT primer being at least 15 nucleotides in length, corresponding in sequence to the 3'-end of the bacteriophage-specific promoter, and extending across into at least the first two nucleotides of the cRNA, the mixture including all possibilities for the 3'-terminal two nucleotides;

(2) using the product of transcription in each of the sixteen subpools as a template for a polymerase chain reaction with a 3'-PCR primer that corresponds in sequence to a sequence vector adjoining the site of insertion of the cDNA sample in the vector and a 5'-PCR primer selected from the group consisting of: (i) the 5'-RT primer from which first-strand cDNA was made for that subpool; (ii) the 5'-RT primer from which the first-strand cDNA was made for that subpool extended at its 3'-terminus by an additional residue -N, where N can be any of A, C, G, or T; and (iii) the 5'-RT primer used for the synthesis of first-strand cDNA for that subpool extended at its 3'-terminus by two additional residues -N-N, wherein N can be any of A, C, G, or T, to produce polymerase chain reaction amplified fragments; and (3) resolving the polymerase chain reaction amplified fragments by electrophoresis to display bands representing the 3'-ends of mRNAs present in the sample.

In another preferred embodiment, the method comprises:

(1) dividing the cRNA preparation into subpools and transcribing first-strand cDNA from each subpool, using a reverse transcriptase and one of the 5'-RT primers defined as having a 3'-terminus consisting of -$N_x$, wherein "N" is one of the four deoxyribonucleotides A, C, G, or T, and "x" is an integer from 1 to 5, the 5'-RT primer being 15 to 30 nucleotides in length and complementary to the 5' flanking vector sequence with the 5'-RT primer's complementarity extending across into the insert-specific nucleotides of the cRNA in a number of nucleotides equal to "x", wherein a different one of said 5'-RT primers is used in different subpools and wherein there are 4 subpools if "x"=1, 16 subpools if "x"=2, 64 subpools if "x"=3, 256 subpools if "x"=4, and 1,024 subpools if "x"=5;

(2) using the product of first-strand cDNA transcription in each of the subpools as a template for a polymerase chain reaction with a 3'-PCR primer of 15 to 30 nucleotides in length that is complementary to 3' flanking vector sequences between said first restriction endonuclease site and the site defining tanscription initiation by the bacteriophage-specific promoter and a 5'-PCR primer having a 3'-terminus consisting of $-N_x-N_y$, where "N" and "x" are as in step (f), $-N_x$ is the same sequence as in the 5'-RT primer from which first-strand cDNA was made for that subpool, and "y" is a whole integer such that x+y equals an integer selected from the group consisting of 3, 4, 5 and 6, the 5'-PCR primer being 15 to 30 nucleotides in length and complementary to the 5' flanking vector sequence with the 5'-PCR primer's complementarity extending across into the insert-specific nucleotides of the cRNA in a number of nucleotides equal to "x+y", to produce polymerase chain reaction amplified fragments; and (3) resolving the polymerase chain reaction amplified fragments to generate a display of sequence-specific products representing the 3'-ends of different mRNAs present in the mRNA population.

Yet another aspect of the present invention is a method for detecting a change in the pattern of mRNA expression in a tissue associated with a physiological or pathological change. This method comprises the steps of:

(1) obtaining a first sample of a tissue that is not subject to the physiological or pathological change;

(2) determining the pattern of mRNA expression in the first sample of the tissue by performing steps (1)–(3) of the method described above for simultaneous sequence-specific identification of mRNAs corresponding to members of an antisense cRNA pool representing the 3'-ends of a population of mRNAs to generate a first display of bands representing the 3'-ends of mRNAs present in the first sample;

(3) obtaining a second sample of the tissue that has been subject to the physiological or pathological change;

(4) determining the pattern of mRNA expression in the second sample of the tissue by performing steps (1)–(3) of the method described above for simultaneous sequence-specific identification of mRNAs corresponding to members of an antisense cRNA pool to generate a second display of bands representing the 3'-ends of mRNAs present in the second sample; and (5) comparing the first and second displays to determine the effect of the physiological or pathological change on the pattern of mRNA expression in the tissue.

The comparison is typically made in adjacent lanes.

The tissue can be derived from the central nervous system or from particular structures within the central nervous system. The tissue can alternatively be derived from another organ or organ system.

Another aspect of the present invention is a method of screening for a side effect of a drug. The method can comprise the steps of:

(1) obtaining a first sample of tissue from an organism treated with a compound of known physiological function;

(2) determining the pattern of mRNA expression in the first sample of the tissue by performing steps (1)–(3) of the method described above for simultaneous sequence-specific identification of mRNAs corresponding to members of an antisense cRNA pool to generate a first display of bands representing the 3'-ends of mRNAs present in the first sample;

(3) obtaining a second sample of tissue from an organism treated with a drug to be screened for a side effect;

(4) determining the pattern of mRNA expression in the second sample of the tissue by performing steps (1)–(3) of the method described above for simultaneous sequence-specific identification of mRNAs corresponding to members of an antisense cRNA pool to generate a second display of bands representing the 3'-ends of mRNAs present in the second sample; and (5) comparing the first and second displays in order to detect the presence of mRNA species whose expression is not affected by the known compound but is affected by the drug to be screened, thereby indicating a difference in action of the drug to be screened and the known compound and thus a side effect.

The drug to be screened can be a drug affecting the central nervous system, such as an antidepressant, a neuroleptic, a tranquilizer, an anticonvulsant, a monoamine oxidase inhibitor, or a stimulant. Alternatively, the drug can be another class of drug such as an anti-parkinsonism agent, a skeletal muscle relaxant, an analgesic, a local anesthetic, a cholinergic, an antispasmodic, a steroid, or a non-steroidal anti-inflammatory drug.

Another aspect of the present invention is panels of primers and degenerate mixtures of primers suitable for the practice of the present invention. These include:

(1) a panel of 5'-RT primers comprising 16 primers of the sequence A-G-G-T-C-G-A-C-G-G-T-A-T-C-G-G-N-N (SEQ ID NO: 3), wherein N is one of the four deoxyribonucleotides A, C, G, or T;

(2) a panel of 5'-RT primers comprising 64 primers of the sequences A-G-G-T-C-G-A-C-G-G-T-A-T-C-G-G-N-N-N (SEQ ID NO: 5), wherein N is one of the four deoxyribonucleotides A, C, G, or T;

(3) a panel of 5'-PCR primers comprising 256 primers of the sequences A-G-G-T-C-G-A-C-G-G-T-A-T-C-G-G-N-N-N-N (SEQ ID NO: 6), wherein N is one of the four deoxyribonucleotides A, C, G, or T; and (4) a panel of 5'-PCR primers comprising 1024 primers of the sequences A-G-G-T-C-G-A-C-G-G-T-A-T-C-G-G-N-N-N-N-N (SEQ ID NO: 24), wherein N is one of the four deoxyribonucleotides A, C, G, or T; and (5) a panel of 5'-PCR primers comprising 4096 primers of the sequences A-G-G-T-C-G-A-C-G-G-T-A-T-C-G-G-N-N-N-N-N-N (SEQ ID NO: 25), wherein N is one of the four deoxyribonucleotides A, C, G, or T; and (6) a panel of anchor primers comprising 12 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-T-V-N (SEQ ID NO: 2), wherein V is a deoxyribonucleotide selected from the group consisting of A, C, and G; and N is a deoxyribonucleotide selected from the group consisting of A, C, G, and T;

(7) a panel of anchor primers comprising 3 primers of the sequences A-A-C-T-G-G-A-A-G-A-A-T-T-C-G-C-G-G-C-C-C-A-G-G-A-A-T-T-T-T-T-T-T-T-T-T-T-T-T-T-T-T-T-V (SEQ ID NO: 23), wherein V is a deoxyribonucleotide selected from the group consisting of A, C, and G;

(8) a panel of 5'-RT primers comprising 4 different oligonucleotides each having the sequence G-G-T-C-

G-A-C-G-G-T-A-T-C-G-G-N (SEQ ID NO: 9), wherein N is one of the four deoxyribonucleotides A, C, G, or T;

(9) a panel of 5'-RT primers comprising 16 different oligonucleotides each having the sequence G-T-C-G-A-C-G-G-T-A-T-C-G-G-N-N (SEQ ID NO: 7), wherein N is one of the four deoxyribonucleotides A, C, G, or T;

(10) a panel of 5'-PCR primers comprising 64 different oligonucleotides each having the sequence T-C-G-A-C-G-G-T-A-T-C-G-G-N-N-N (SEQ ID NO: 13), wherein N is one of the four deoxyribonucleotides A, C, G, or T;

(11) a panel of 5'-PCR primers comprising 256 different oligonucleotides each having the sequence C-G-A-C-G-G-T-A-T-C-G-G-N-N-N-N (SEQ ID NO: 14), wherein N is one of the four deoxyribonucleotides A, C, G, or T;

(12) a panel of 5'PCR primers comprising 1024 different oligonucleotides each having the sequence G-A-C-G-G-T-A-T-C-G-G-N-N-N-N-N (SEQ ID NO: 15), wherein N is one of the four deoxyribonucleotides A, C, G, or T;

(13) a panel of 5'-PCR primers comprising 4096 different oligonucleotides each having the sequence A-C-G-G-T-A-T-C-G-G-N-N-N-N-N-N (SEQ ID NO: 16), wherein N is one of the four deoxyribonucleotides A, C, G, or T;

(14) a panel of 5'-RT primers comprising 4 different oligonucleotides each having the sequence C-T-T-C-A-G-T-C-A-G-G-C-T-A-A-T-C-G-G-N (SEQ ID NO: 10), wherein N is one of the four deoxyribonucleotides A, C, G, or T;

(15) a panel of 5'-RT primers comprising 16 different oligonucleotides each having the sequence T-T-C-A-G-T-C-A-G-G-C-T-A-A-T-C-G-G-N-N (SEQ ID NO: 11), wherein N is one of the four deoxyribonucleotides A, C, G, or T;

(16) a panel of 5'-PCR primers comprising 64 different oligonucleotides each having the sequence T-C-A-G-T-C-A-G-G-C-T-A-A-T-C-G-G-N-N-N (SEQ ID NO: 12), wherein N is one of the four deoxyribonucleotides A, C, G, or T;

(17) a panel of 5'-PCR primers comprising 256 different oligonucleotides each having the sequence C-A-G-T-C-A-G-G-C-T-A-A-T-C-G-G-N-N-N-N (SEQ ID NO: 17), wherein N is one of the four deoxyribonucleotides A, C, G, or T;

(18) a panel of 5'-PCR primers comprising 1024 different oligonucleotides each having the sequence A-G-T-C-A-G-G-C-T-A-A-T-C-G-G-N-N-N-N-N (SEQ ID NO: 26), wherein N is one of the four deoxyribonucleotides A, C, G, or T;

(19) a panel of 5'-PCR primers comprising 4096 different oligonucleotides each having the sequence G-T-C-A-G-G-C-T-A-A-T-C-G-G-N-N-N-N-N-N (SEQ ID NO: 27), wherein N is one of the four deoxyribonucleotides A, C, G, or T;

(20) a degenerate mixture of anchor primers comprising a mixture of 3 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-V (SEQ ID NO: 23), wherein V is a deoxyribonucleotide selected from the group consisting of A, C, and G, each of the 3 primers being present in about an equimolar quantity; and

(21) a degenerate mixture of anchor primers comprising a mixture of 12 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-V-N (SEQ ID NO: 2), wherein V is a deoxyribonucleotide selected from the group consisting of A, C, and G; and N is a deoxyribonucleotide selected from the group consisting of A, C, G, and T, each of the 12 primers being present in about an equimolar quantity.

BRIEF DESCRIPTION OF THE DRAWINGS

These and other features, aspects, and advantages of the present invention will become better understood with reference to the following description, appended claims, and accompanying drawings where:

FIGS. 3A–3C shows the nucleotide sequence of the multiple cloning sites of plasmids pBS SK+/DGT1 (SEQ ID NO:20, FIG. 3A), pBS SK+/DGT2 (SEQ ID NO:21, FIG. 3B), and pBS SK+/DGT3 (SEQ ID NO:22, FIG. 3C).

DESCRIPTION

Figure 1:
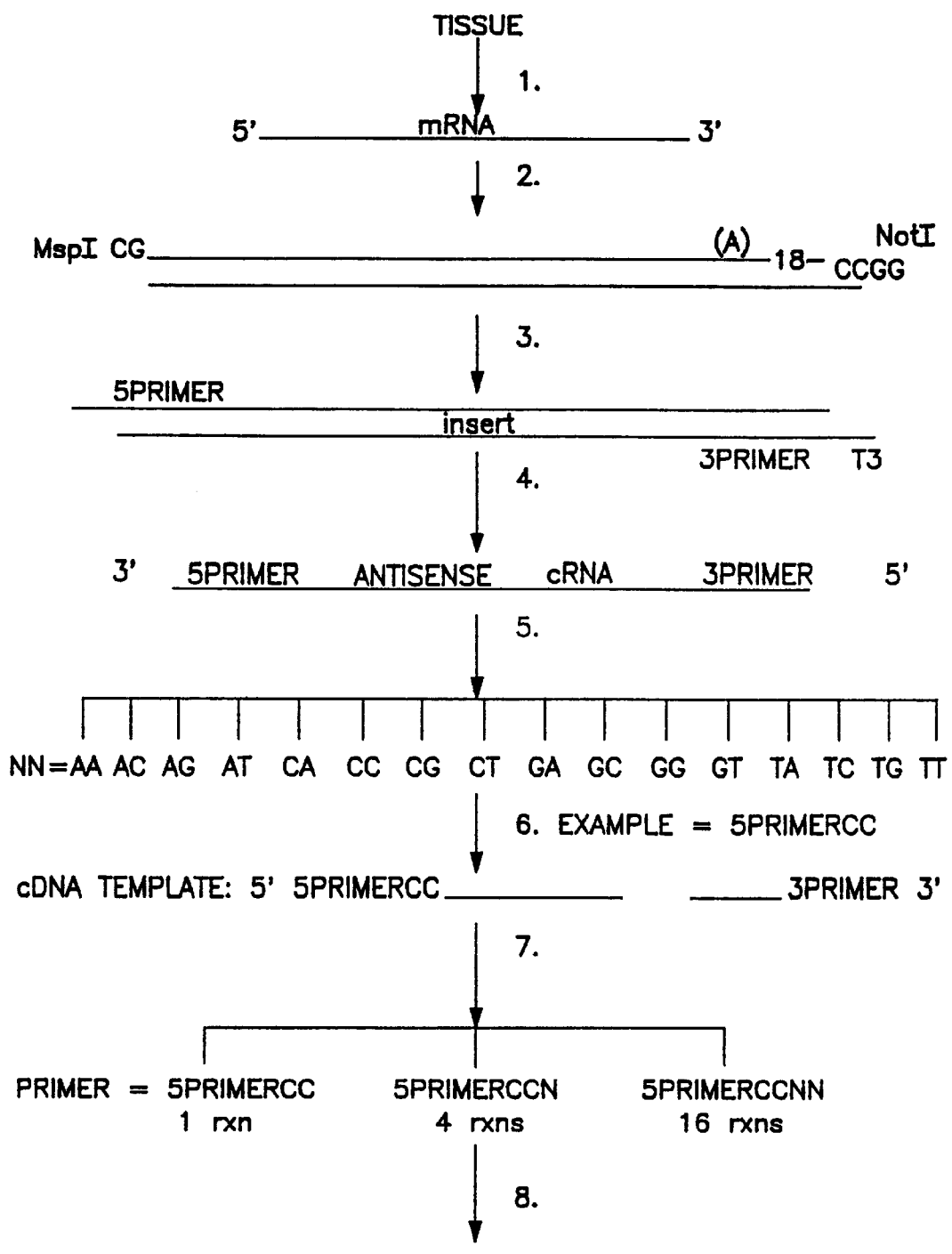
FIG. 1 is a diagrammatic depiction of the method of the present invention showing the various stages of priming, cleavage, cloning and amplification.

We have developed a method for simultaneous sequence-specific identification and display of mRNAs in a mRNA population.

As discussed below, this method has a number of applications in drug screening, the study of physiological and pathological conditions, and genomic mapping. These applications will be discussed below.

Simultaneous Sequence-specific Identification of mRNAs

A method according to the present invention, based on the polymerase chain reaction (PCR) technique, provides means for visualization of nearly every mRNA expressed by a tissue as a distinct band on a gel whose intensity corresponds roughly to the concentration of the mRNA. The method is based on the observation that virtually all mRNAs conclude with a 3'-poly (A) tail but does not rely on the specificity of primer binding to the tail.

In general, the method comprises:

(1) preparing double-stranded cDNAs from a mRNA population using a mixture of 12 anchor primers, the anchor primers each including: (i) a tract of from 7 to 40 T residues; (ii) a site for cleavage by a first restriction endonuclease that recognizes more than six bases, the site for cleavage being located to the 5'-side of the tract of T residues; (iii) a first stuffer segment of from 4 to 40 nucleotides, the first stuffer segment being located to the 5'-side of the site for cleavage by the restriction endonuclease; and (iv) phasing residues -V-N located at the 3' end of each of the anchor primers, wherein V is a deoxyribonucleotide selected from the group consisting of A, C, and G; and N is a deoxyribonucleotide selected from the group consisting of A, C, G, and T, the mixture including anchor primers containing all possibilities for V and N;

(2) producing cloned inserts from a suitable host cell that has been transformed by a vector, the vector having the cDNA sample that has been cleaved with a first restriction endonuclease and a second restriction endonuclease inserted therein, the cleaved cDNA sample being inserted in the vector in an orientation that is antisense with respect to a bacteriophage-specific promoter within the vector, the second restriction endonuclease recognizing a four-nucleotide sequence and the first restriction endonuclease cleaving at a single site within each member of the mixture of anchor primers;

(3) generating linearized fragments of the cloned inserts by digestion with at least one restriction endonuclease that is different from the first and second restriction endonucleases;

(4) generating a cRNA preparation of antisense cRNA transcripts by incubation of the linearized fragments with a bacteriophage-specific RNA polymerase capable of initiating transcription from the bacteriophage-specific promoter;

(5) dividing the cRNA preparation into sixteen subpools and transcribing first-strand cDNA from each subpool, using a thermostable reverse transcriptase and one of sixteen 5'-RT primers whose 3'-terminus is -N-N, wherein N is one of the four deoxyribonucleotides A, C, G, or T, the 5'-RT primer being at least 15 nucleotides in length, corresponding in sequence to the 3'-end of the bacteriophage-specific promoter, and extending across into at least the first two nucleotides of the cRNA, the mixture including all possibilities for the 3'-terminal two nucleotides;

(6) using the product of transcription in each of the sixteen subpools as a template for a polymerase chain reaction with a 3'-PCR primer that corresponds in sequence to a sequence in the vector adjoining the site of insertion of the cDNA sample in the vector and a 5'-PCR primer selected from the group consisting of: (i) the 5'-RT primer from which first-strand cDNA was made for that subpool; (ii) the 5'-RT primer from which the first-strand cDNA was made for that subpool extended at its 3'-terminus by an additional residue -N, where N can be any of A, C, G, or T; and (iii) the 5'-RT primer used for the synthesis of first-strand cDNA for that subpool extended at its 3'-terminus by two additional residues -N-N, wherein N can be any of A, C, G, or T, to produce polymerase chain reaction amplified fragments; and (7) resolving the polymerase chain reaction amplified fragments by electrophoresis to display bands representing the 3'-ends of mRNAs present in the sample. A depiction of this scheme is shown in FIG. 1.

In another embodiment, the method comprises the steps of:

(a) preparing a double-stranded cDNA population from an mRNA population using a mixture of anchor primers, the anchor primers each including: (i) a tract of from 7 to 40 T residues; (ii) a site for cleavage by a first restriction endonuclease that recognizes more than six bases, the site for cleavage being located to the 5'-side of the tract of T residues; (iii) a first stuffer segment of from 4 to 40 nucleotides, the first stuffer segment being located to the 5'-side of the site for cleavage by the first restriction endonuclease; and (iv) phasing residues located at the 3' end of each of the anchor primers selected from the group consisting of -V and -V-N, wherein V is a deoxyribonucleotide selected from the group consisting of A, C, and G; and N is a deoxyribonucleotide selected from the group consisting of A, C, G, and T, the mixture including anchor primers containing all possibilities for V and N where the phasing residues in the mixture are defined by one of -V, or -V-N;

(b) cleaving the double-stranded cDNA population with the first restriction endonuclease and with a second restriction endonuclease, the second restriction endonuclease recognizing a four-nucleotide sequence, to form a population of double-stranded cDNA molecules having first and second termini, respectively;

(c) inserting the double-stranded cDNA molecules from step (b) each into a vector in an orientation that is antisense with respect to a bacteriophage-specific promoter within the vector to form a population of vectors containing the inserted cDNA molecules, said inserting defining 3' and 5' flanking vector sequences such that 5' is upstream from the sense strand of the inserted cDNA and 3' is downstream of the sense strand, and said vector having a 3' flanking nucleotide sequence of from at least 15 nucleotides in length between said first restriction endonuclease site and a site defining transcription initiation in said promoter;

(d) generating linearized fragments containing the inserted cDNA molecules by digestion of the vectors produced in step (c) with at least one restriction endonuclease that does not recognize sequences in the inserted cDNA molecules or in the bacteriophage-specific promoter, but does recognize sequences in the vector such that the resulting linearized fragments have a 5' flanking vector sequence of at least 15 nucleotides 5' to the site of insertion of the cDNA sample into the vector at the cDNA's second terminus;

(e) generating a cRNA preparation of antisense cRNA transcripts by incubation of the linearized fragments with a bacteriophage-specific RNA polymerase capable of initiating transcription from the bacteriophage-specific promoter;

(f) dividing the cRNA preparation into subpools and transcribing first-strand cDNA from each subpool, using a reverse transcriptase and one of the 5'-RT primers defined as having a 3'-terminus consisting of -$N_x$, wherein "N" is one of the four deoxyribonucleotides A, C, G, or T, and "x" is an integer from 1 to 5, the 5'-RT primer being 15 to 30 nucleotides in length and complementary to the 5' flanking vector sequence with the 5'-RT primer's complementarity extending across into the insert-specific nucleotides of the cRNA in a number of nucleotides equal to "x", wherein a different one of said 5'-RT primers is used in different subpools and wherein there are 4 subpools if "x"=1, 16 subpools if "x"2, 64 subpools if "x"=3, 256 subpools if "x"4, and 1,024 subpools if "x"=5;

(g) using the product of first-strand cDNA transcription in each of the subpools as a template for a polymerase chain reaction with a 3'-PCR primer of 15 to 30 nucleotides in length that is complementary to 3' flanking vector sequences between said first restriction endonuclease site and the site defining transcription initiation by the bacteriophage-specific promoter and a 5'-PCR primer having a 3'-terminus consisting of -$N_x$-$N_y$, where "N" and "x" are as in step (f), -$N_x$ is the same sequence as in the 5'-RT primer from which first-strand cDNA was made for that subpool, and "y" is a whole integer such that x+y equals an integer selected from the group consisting of 3, 4, 5 and 6, the 5-PCR primer being 15 to 30 nucleotides in length and complementary to the 5' flanking vector sequence with the 5'-PCR primer's complementarity extending across into the insert-specific nucleotides of the cRNA in a number of nucleotides equal to "x+y", to produce polymerase chain reaction amplified fragments; and (h) resolving the polymerase chain reaction amplified fragments to generate a display of sequence-specific products representing the 3'-ends of different mRNAs present in the mRNA population.

A. Isolation of mRNA

The first step in the method is isolation or provision of a mRNA population. Methods of extraction of RNA are well-known in the art and are described, for example, in J. Sambrook et al., "Molecular Cloning: A Laboratory Manual" (Cold Spring Harbor Laboratory Press, Cold Spring Harbor, N.Y., 1989), vol. 1, ch. 7, "Extraction, Purification, and Analysis of Messenger RNA from Eukaryotic Cells," incorporated herein by this reference. Other isolation and extraction methods are also well-known. Typically, isolation is performed in the presence of chaotropic agents such as guanidinium chloride or guanidinium thiocyanate, although other detergents and extraction agents can alternatively be used.

Typically, the mRNA is isolated from the total extracted RNA by chromatography over oligo(dT)-cellulose or other chromatographic media that have the capacity to bind the polyadenylated 3'-portion of mRNA molecules. Alternatively, but less preferably, total RNA can be used. However, it is generally preferred to isolate poly(A)$^+$ RNA.

B. Preparation of Double-Stranded cDNA

Double-stranded cDNAs are then prepared from the mRNA population using a mixture of anchor primers to initiate reverse tanscription. The anchor primers each include: (i) a tract of from 7 to 40 T residues; (ii) a site for cleavage by a restriction endonuclease that recognizes more than six bases, the site for cleavage being located to the 5'-side of the tract of T residues; (iii) a first stuffer segment of from 4 to 40 nucleotides, the first stuffer segment being located to the 5'-side of the site for cleavage by the restriction endonuclease; (iv) a second stuffer segment of zero to eight residues interposed between the site for cleavage by a restriction endonuclease that recognizes more than six bases and the tract of T residues; and (v) phasing residues chosen from the group consisting of -V and -V-N located at the 3' end of each of the anchor primers, wherein V is a deoxyribonucleotide selected from the group consisting of A, C, and G; and N is a deoxyribonucleotide selected from the group consisting of A, C, G, and T. The mixture includes anchor primers containing all possibilities for V and N. Where the anchor primers have phasing residues of -V, the mixture comprises a mixture of three anchor primers. Where the anchor primers have phasing residues of -V-N, the mixture comprises a mixture of twelve anchor primers.

Typically, the anchor primers each have 18 T residues in the tract of T residues, and the first stuffer segment of the anchor primers is 14 residues in length. A suitable sequence of the first stuffer segment is A-A-C-T-G-G-A-A-G-A-A-T-T-C (SEQ ID NO: 1). Typically, the site for cleavage by a restriction endonuclease that recognizes more than six bases is the NotI cleavage site. One preferred set of three anchor primers has the sequence A-A-C-T-G-G-A-A-G-A-A-T-T-C-G-C-G-G-C-C-G-C-A-G-G-A-A-T-T-T-T-T-T-T-T-T-T-T-T-T-T-T-T-T-T-V (SEQ ID NO: 23). Another preferred set of twelve anchor primers has the sequence A-A-C-T-G-G-A-A-G-A-A-T-T-C-G-C-G-G-C-C-G-C-A-G-G-A-A-T-T-T-T-T-T-T-T-T-T-T-T-T-T-T-T-T-V-N (SEQ ID NO: 2).

One member of this mixture of anchor primers initiates synthesis at a fixed position at the 3'-end of all copies of each mRNA species in the sample, thereby defining a 3'-end point for each species.

This reaction is carried out under conditions for the preparation of double-stranded cDNA from mRNA that are well-known in the art. Such techniques are described, for example, in Volume 2 of J. Sambrook et al., "Molecular Cloning: A Laboratory Manual", entitled "Construction and Analysis of cDNA Libraries." Suitable reverse transcriptases include those from avian myeloblastosis virus (AMV) and Maloney murine leukemia virus (MMLV). A preferred reverse transcriptase is the MMLV reverse transcriptase.

C. Cleavage of the cDNA Sample with Restriction Endonucleases

The cDNA sample is cleaved with two restriction endonucleases. The first restriction endonuclease recognizes a site longer than six bases and cleaves at a single site within each member of the mixture of anchor primers. The second restriction endonuclease is an endonuclease that recognizes a 4-nucleotide sequence. Such endonucleases typically cleave at multiple sites in most cDNAs. Typically, the first restriction endonuclease is NotI and the second restriction endonuclease is MspI. The enzyme NotI does not cleave within most cDNAs. This is desirable to minimize the loss of cloned inserts that would result from cleavage of the cDNAs at locations other than in the anchor site.

Alternatively, the second restriction endonuclease can be TaqI, MaeII or HinP1I. The use of the latter two restriction endonucleases can detect mRNAs that are not cleaved by MspI. The second restriction endonuclease generates a 5'-overhang compatible for cloning into the desired vector, as discussed below. This cloning, for the vector chosen from the group consisting of pBC SK$^+$, pBS SK$^+$, pBS SK$^+$/DGT1, pBS SK$^+$/DGT2 and pBS SK$^+$/DGT3, is into the ClaI site, as discussed below.

Alternatively, other suitable restriction endonucleases can be used to detect cDNAs not cleaved by the above restriction endonucleases. In such embodiments, suitable first restriction endonucleases that recognize more than six bases are AscI, BaeI, FseI, NotI, PacI, PmeI, PpuMI, RsrII, SapI, SexAI, SfiI, SgfI, SgrAI, SrfI, Sse8387I and SwaI. Suitable second restriction endonucleases recognizing a four-nucleotide sequence are MboI, DpnII, Sau3AI, Tsp509I, HpaII, BfaI, Csp$_6$I, MseI, HhaI, NlaIII, TaqI, MspI, MaeII and HinP1I.

Conditions for digestion of the cDNA are well-known in the art and are described, for example, in J. Sambrook et al., "Molecular Cloning: A Laboratory Manual," Vol. 1, Ch. 5, "Enzymes Used in Molecular Cloning."

Insertion of Cleaved cDNA into a Vector

The cDNA sample cleaved with the first and second restriction endonucleases is then inserted into a vector. In general, a suitable vector includes a multiple cloning site having a NotI restriction endonuclease site. A suitable vector is the plasmid pBC SK$^+$ that has been cleaved with the restriction endonucleases ClaI and NotI. The vector contains a bacteriophage-specific promoter. Typically, the promoter is a T3 promoter, a SP6 promoter, or a T7 promoter. A preferred promoter is bacteriophage T3 promoter. The cleaved cDNA is inserted into the promoter in an orientation that is antisense with respect to the bacteriophage-specific promoter.

In another preferred embodiment, the vector contains at least one bacteriophage promoter chosen from the group consisting of T3 promoter, T7 promotor and SP6 promotor. In one especially preferred embodiment, the vector contains a T3 promoter. In a preferred embodiment, the vector includes a multiple cloning site having a nucleotide sequence chosen from the group consisting of SEQ ID NO: 20, SEQ ID NO: 21 and SEQ ID NO: 22.

Preferred vectors are based on the plasmid vector pBluescript (pBS or pBC) SK+ (Stratagene) in which a portion of the nucleotide sequence from positions 656 to 764 was removed and replaced with a sequence of at least 110 nucleotides including a NotI restriction endonuclease site. This region, designated the multiple cloning site (MCS), spans the portion of the nucleotide sequence from the SacI site to the KpnI site.

A suitable plasmid vector, such as pBC SK+ or pBS SK+ (Stratagene), was digested with suitable restriction endonuclease to remove at least 100 nucleotides of the multiple cloning site. In the case of pBS SK+, suitable restriction endonucleases for removing the multiple cloning site are SacI and KpnI. A cDNA portion comprising a new multiple cloning site, having ends that are compatible with NotI and claI after digestion with first and second restriction endonucleases was cloned into the vector to form a suitable plasmid vector. Preferred cDNA portions comprising new multiple cloning sites include those having the nucleotide sequences described in SEQ ID NO: 20, SEQ ID NO: 21 and SEQ ID NO: 22. cDNA clones are linearized by digestion with a single restriction endonuclease that recognizes the 4-nucleotide sequence of the second restriction endonuclease site.

A preferred plasmid vector, referred to herein as pBS SK+/DGT1, comprises the MCS of SEQ ID NO:20. The pairs for second restriction endonuclease and linearization restriction endonuclease are, respectively: MspI and SmaI; HinP1I and NarI; TaqI and XhoI; MaeII and AatII.

Another preferred plasmid vector, referred to herein as pBS SK+/DGT2, comprises the MCS of SEQ ID NO:21, and was prepared as described above for pBS SK+/DGT1. For pBS SK+/DGT2, the pairs for second restriction endonuclease and linearization restriction endonuclease are, respectively: MspI and SmaI; HinP1I and NarI; and TaqI and XhoI.

Another preferred plasmid vector, referred to herein as pBS SK+/DGT3, comprises the MCS of SEQ ID NO:22. The pairs for second restriction endonuclease and linearization restriction endonuclease are, respectively: MspI and SmaI; HinP1I and NarI; TaqI and XhoI; MaeII and AatII.

In a preferred embodiment the vector includes a vector stuffer sequence that comprises an internal vector stuffer restriction endonuclease site between the first and second vector restriction endonuclease sites. In one such an embodiment, the linearization step includes digestion of the vector with a restriction endonuclease which cleaves the vector at the internal vector stuffer restriction endonuclease site. In another such embodiment, the restriction endonuclease used in the linearization step also cleaves the vector at the internal vector stuffer restriction endonuclease site.

E. Transformation of a Suitable Host Cell

The vector into which the cleaved DNA has been inserted is then used to transform a suitable host cell that can be efficiently transformed or transfected by the vector containing the insert. Suitable host cells for cloning are described, for example, in Sambrook et al., "Molecular Cloning: A Laboratory Manual," supra. Typically, the host cell is prokaryotic. A particularly suitable host cell is a strain of *E. coli*. A suitable *E. coli* strain is MC1061. Preferably, a small aliquot is also used to transform *E. coli* strain XL1-Blue so that the percentage of clones with inserts is determined from the relative percentages of blue and white colonies on X-gal plates. Only libraries with in excess of $5\times10^5$ recombinants are typically acceptable.

F. Generation of Linearized Fragments

Plasmid preparations, typically as minipreps, are then made from each of the cDNA libraries. Linearized fragments are then generated by digestion with at least one restriction endonuclease.

In one embodiment, vector is the plasmid pBC SK+ and MspI is used both as the second restriction endonuclease and as the linearization restriction endonuclease.

In another embodiment, vector is the plasmid pBC SK+, the second restriction endonuclease is chosen from the group consisting of MspI, MaeII, TaqI and HinP1I and the linearization is accomplished by a first digestion with SmaI followed by a second digestion with a mixture of KpnI and ApaI.

In other embodiments the vector is chosen from the group consisting of pBS SK+/DGT1, pBS SK+/DGT2 and pBS SK+/DGT3. In such embodiments, one suitable enzyme combination is provided where the second restriction endonuclease is MspI and the restriction endonuclease used in the linearization step is SmaI. Another suitable combination is provided where the second restriction endonuclease is TaqI and the restriction endonuclease used in the linearization step is XhoI. A further suitable combination is provided where the second restriction endonuclease is HinP1I and the restriction endonuclease used in the linearization step is NarI. Yet another suitable combination is provided where the second restriction endonuclease is MaeII and the restriction endonuclease used in the linearization step is AatII. In general, in the linearization step, described in detail in Section F, below, any plasmid vector lacking the cDNA insert was cleaved at the 6-nucleotide recognition site (underlined in FIG. 3A) for SmaI, NarI, XhoI, or AatII found between the NotI site and the ClaI site. In contrast, plasmid vectors containing inserts would be cleaved at the 6-nucleotide recognition site for SmaI, NarI, XhoI or AatII sites found 3' to the ClaI site.

In another embodiment, an aliquot of each of the cloned inserts is divided into two pools, one of which is cleaved with XhoI and the second with SalI. The pools of linearized plasmids are combined, mixed, then divided into thirds. The thirds are digested with HindIII, BamHI, and EcoRI. This procedure is followed because, in order to generate antisense transcripts of the inserts with T3 RNA polymerase, the template must first be cleaved with a restriction endonuclease that cuts within flanking sequences but not within the inserts themselves. Given that the average length of the 3'-terminal MspI fragments is 256 base pairs, approximately 6% of the inserts contain sites for any enzyme with a hexamer recognition sequence. Those inserts would be lost to further analysis were only a single enzyme utilized. Hence, it is preferable to divide the reaction so that only one of either of two enzymes is used for linearization of each half reaction. Only inserts containing sites for both enzymes (approximately 0.4%) are lost from both halves of the samples. Similarly, each cRNA sample is contaminated to a different extent with transcripts from insertless plasmids, which could lead to variability in the efficiency of the later polymerase chain reactions for different samples because of differential competition for primers. Cleavage of thirds of the samples with one of three enzymes that have single targets in pBC SK+ between its ClaI and NotI sites eliminates the production of transcripts containing binding sites for the eventual 5' primers in the PCR process from insertless plasmids. The use of three enzymes on thirds of the reaction reduces the use of insert-containing sequences that also contain sites for the enzyme while solving the problem of possible contamination of insertless sequences. If only one enzyme were used, about 10% of the insert-containing sequences would be lost, but this is reduced to about 0.1%, because only those sequences that fail to be cleaved by all three enzymes are lost.

G. Generation of cRNA

The next step is a generation of a cRNA preparation of antisense cRNA transcripts. This is performed by incubation of the linearized fragments with an RNA polymerase capable of initiating transcription from the bacteriophage-specific promoter. Typically, as discussed above, the promoter is a T3 promoter, and the polymerase is therefore T3 RNA polymerase. The polymerase is incubated with the linearized fragments and the four ribonucleoside triphosphates under conditions suitable for synthesis.

H. Transcription of First-Strand cDNA

In a preferred embodiment, the cRNA preparation is divided into a number of subpools, the number depending on the number of phasing residues of the 5'-RT primer. First-strand cDNA is then transcribed from each subpool, using Maloney murine leukemia virus (MMLV) reverse transcriptase (Life Technologies). With this reverse transcriptase annealing is performed at 42° C., and the transcription reaction at 42° C. The reaction in each subpool uses one of the 5'-RT primers defined as having a 3'-terminus consisting of -N$_x$, wherein "N" is one of the four deoxyribonucleotides A, C, G, or T, and "x" is an integer from 1 to 5, the 5'-RT primer being 15 to 30 nucleotides in length and complementary to the 5' flanking vector sequence with the 5'-RT primer's complementarity extending across into the insert-specific nucleotides of the cRNA in a number of nucleotides equal to "x", wherein a different one of said 5'-RT primers is used in different subpools and wherein there are 4 subpools if "x"=1, 16 subpools if "x"=2, 64 subpools if "x"=3, 256 subpools if "x"=4, and 1,024 subpools if "x"=5.

In another embodiment, the cRNA preparation is divided into sixteen subpools. First-strand cDNA is then transcribed from each subpool, using a thermostable reverse transcriptase and a 5'-RT primer as described below. A preferred transcriptase is the recombinant reverse transcriptase from *Thermus thermophilus*, known as rTth, available from Perkin-Elmer (Norwalk, Conn.). This enzyme is also known as an RNA-dependent DNA polymerase. With this reverse transcriptase, annealing is performed at 60° C., and the transcription reaction at 70° C. This promotes high fidelity complementarity between the 5'-RT primer and the cRNA. The 5'-RT primer used is one of the sixteen 5'-RT primers whose 3'-terminus is -N-N, wherein N is one of the four deoxyribonucleotides A, C, G, or T, the 5'-RT primer being at least 15 nucleotides in length, corresponding in sequence to the 3'-end of the bacteriophage-specific promoter, and extending across into at least the first two nucleotides of the cRNA.

Where the bacteriophage-specific promoter is the T3 promoter, the 5'-RT primers typically have the sequence A-G-G-T-C-G-A-C-G-G-T-A-T-C-G-G-N-N (SEQ ID NO: 3), A-G-G-T-C-G-A-C-G-G-T-A-T-C-G-G-N-N-N (SEQ ID NO: 5), A-G-G-T-C-G-A-C-G-G-T-A-T-C-G-G-N-N-N-N (SEQ ID NO: 6), G-G-T-C-G-A-C-G-G-T-A-T-C-G-G-N (SEQ ID NO: 9), G-T-C-G-A-C-G-G-T-A-T-C-G-G-N-N (SEQ ID NO: 7), T-C-G-A-C-G-G-T-A-T-C-G-G-N-N-N-N (SEQ ID NO: 13), C-G-A-C-G-G-T-A-T-C-G-G-N-N-N-N (SEQ ID NO: 14), G-A-C-G-G-T-A-T-C-G-G-N-N-N-N-N (SEQ ID NO: 15), or A-G-G-T-C-G-A-C-G-G-T-A-T-C-G-G-N-N-N-N-N (SEQ ID NO: 24).

I. PCR Reaction

The next step is the use of the product of transcription in each of the subpools as a template for a polymerase chain reaction with primers as described below to produce polymerase chain reaction amplified fragments.

In general, the product of first-strand cDNA transcription in each of the subpools is used as a template for a polymerase chain reaction with a 3'-PCR primer and a 5'-PCR primer to produce polymerase chain reaction amplified fragments. The 3'-PCR primer typically is 15 to 30 nucleotides in length, and is complementary to 3' flanking vector sequences between the first restriction endonuclease site and the site defining transcription initiation by the bacteriophage-specific promoter. The 5'-PCR primers have a 3'-terminus consisting of -N$_x$-N$_y$, where "N" and "x" are as in reverse transcriptase step above, -N$_x$ is the same sequence as in the 5'-RT primer from which first-strand cDNA was made for that subpool, and "y" is a whole integer such that x+y equals an integer selected from the group consisting of 3, 4, 5 and 6, the 5'-PCR primer being 15 to 30 nucleotides in length and complementary to the 5' flanking vector sequence with the 5'-PCR primer's complementarity extending across into the insert-specific nucleotides of the cRNA in a number of nucleotides equal to "x+y".

In another embodiment, the primers used are: (a) a 3'-PCR primer that corresponds in sequence to a sequence in the vector adjoining the site of insertion of the cDNA sample in the vector; and (b) a 5'-PCR primer selected from the group consisting of: (i) the 5'-RT primer from which first-strand cDNA was made for that subpool; (ii) the 5'-RT primer from which the first-strand cDNA was made for that subpool extended at its 3'-terminus by an additional residue -N, where N can be any of A, C, G, or T; and (iii) the 5'-RT primer used for the synthesis of first-strand cDNA for that subpool extended at its 3'-terminus by two additional residues -N-N, wherein N can be any of A, C, G, or T.

When the vector is the plasmid pBC SK$^+$ cleaved with ClaI and NotI, a suitable 3'-PCR primer is G-A-A-C-A-A-A-A-G-C-T-G-G-A-G-C-T-C-C-A-C-C-G-C (SEQ ID NO: 4). In another embodiment, where the vector is the plasmid pBC SK$^+$ cleaved with ClaI and NotI, a suitable 3'-PCR primer is A-A-G-C-T-G-G-A-G-C-T-C-C-A-C-C (SEQ ID NO: 8). In other embodiments, suitable 3'-PCR primers are G-A-G-C-T-C-C-A-C-C-G-C-G-G-T (SEQ ID NO: 18) and G-A-G-C-T-C-G-T-T-T-T-C-C-C-A-G (SEQ ID NO: 19). Where the bacteriophage-specific promoter is the T3 promoter, a suitable 5'-PCR primer can have the sequences A-G-G-T-C-G-A-C-G-G-T-A-T-C-G-G-N-N-N (SEQ ID NO: 5), A-G-G-T-C-G-A-C-G-G-T-A-T-C-G-G-N-N-N-N (SEQ ID NO: 6), T-C-G-A-C-G-G-T-A-T-C-G-G-N-N-N (SEQ ID NO: 13), C-G-A-C-G-G-T-A-T-C-G-G-N-N-N-N (SEQ ID NO: 14), G-A-C-G-G-T-A-T-C-G-G-N-N-N-N-N (SEQ ID NO: 15), or A-C-G-G-T-A-T-C-G-G-N-N-N-N-N-N (SEQ ID NO: 16).

Typically, PCR is performed in the presence of $^{35}$S-dATP using a PCR program of 15 seconds at 94° C. for denaturation, 15 seconds at 50° C.–62° C. for annealing, and 30 seconds at 72° C. for synthesis on a Perkin-Elmer 9600 apparatus (Perkin-Elmer Cetus, NorwaLk, Conn.). The annealing temperature is optimized for the specific nucleotide sequence of the primer, using principles well known in the art. The high temperature annealing step minimizes artifactual mispriming by the 5'-primer at its 3'-end and promotes high fidelity copying.

Alternatively, the PCR amplification can be carried out in the presence of a $^{32}$P-labeled or $^{33}$P-labeled deoxyribonucleoside triphosphate, such as [$^{32}$P]dCTP or [$^{33}$P]dCTP. However, it is generally preferred to use a $^{35}$S-labeled deoxyribonucleoside triphosphate for maximum resolution. Other detection methods, including nonradioactive labels, can also be used.

The series of reactions produce a number of product pools depending on the chosen 5'-PCR primers. As discussed above, the 5'-PCR primers have a 3'-terminus consisting of -$N_x$-$N_y$, where "N" and "x" are as in reverse transcriptase step above, -$N_x$ is the same sequence as in the 5'-RT primer from which first-strand cDNA was made for that subpool, and "y" is a whole integer such that x+y equals an integer selected from the group consisting of 3, 4, 5 and 6, the 5'-PCR primer being 15 to 30 nucleotides in length and complementary to the 5' flanking vector sequence with the 5'-PCR primer's complementarity extending across into the insert-specific nucleotides of the cRNA in a number of nucleotides equal to "x+y". The number of subpools is determined by x+y: there are 64 subpools if x+y=3, 256 subpools if x+=4, 1,024 subpools if x+y =5, and 4,096 subpools if x+y=6.

The process of the present invention can be extended by using longer sets of 5'-PCR primers extended at their 3'-end by additional nucleotides. For example, a 5'-PCR primer with the 3'-terminus -N-N-N-N-N would give 1024 products and a primer with the 3'-terminus -N-N-N-N-N-N would give 4,096 products.

J. Electrophoresis

The polymerase chain reaction amplified fragments are then resolved by electrophoresis to display bands representing the 3'-ends of mRNAs present in the sample.

Electrophoretic techniques for resolving PCR amplified fragments are well-understood in the art and need not be further recited here. The corresponding products are resolved in denaturing DNA sequencing gels and visualized by autoradiography. For the particular vector system described herein, the gels are run so that the first 90 base pairs run off the bottom, since vector-related sequences increase the length of the cDNAs by 55 base pairs. This number can vary if other vector systems are employed, and the appropriate electrophoresis conditions so that vector-related sequences run off the bottom of the gels can be determined from a consideration of the sequences of the vector involved. Typically, each reaction is run on a separate denaturing gel, so that at least two gels are used. It is preferred to perform a series of reactions in parallel, such as from different tissues, and resolve all of the reactions using the same primer on the same gel. A substantial number of reactions can be resolved on the same gel. Typically, as many as thirty reactions can be resolved on the same gel and compared. As discussed below, this provides a way of determining tissue-specific mRNAs.

Typically, autoradiography is used to detect the resolved cDNA species. However, other detection methods, such as phosphorimaging or fluorescence, can also be used, and may provide higher sensitivity in certain applications.

According to the scheme, the cDNA libraries produced from each of the mRNA samples contain copies of the extreme 3'-ends from the most distal site for MspI to the beginning of the poly(A) tail of all poly(A)$^+$ mRNAs in the starting RNA sample approximately according to the initial relative concentrations of the mRNAs. Because both ends of the inserts for each species are exactly defined by sequence, their lengths are uniform for each species allowing their later visualization as discrete bands on a gel, regardless of the tissue source of the mRNA.

The use of successive steps with lengthening primers to survey the cDNAs essentially act like a nested PCR. These steps enhance quality control and diminish the background that potentially could result from amplification of untargeted cDNAs. In a preferred embodiment, the second reverse transcription step subdivides each cRNA sample into four subpools, utilizing a primer that anneals to the sequences derived from pBC SK$^+$ but extends across the CGG of the non-regenerated MspI site and including one nucleotide (-N) of the insert. This step segregates the starting population of potentially 50,000 to 100,000 mRNAs into four subpools of approximately 12,500 to 25,000 members each. In serial iterations of the subsequent PCR step, in which radioactive label is incorporated into the products for their autoradiographic visualization, those pools are further segregated by division into four or sixteen subsubpools by using progressively longer 5'-PCR primers containing 2–6 nucleotides of the insert.

By first demanding by high temperature annealing a high fidelity 3'-end match at the reverse transcription step in the -N positions, and subsequently demanding again such high fidelity matching into -N-N, -N-N-N, -N-N-N-N, -N-N-N-N-N or -N-N-N-N-N-N iterations, bleedthrough from mismatched priming at the -N positions is drastically minimized.

The steps of the process beginning with dividing the cRNA preparation into four subpools and transcribing first-strand cDNA from each subpool can be performed separately as a method of simultaneous sequence-specific identification of mRNAs corresponding to members of an antisense cRNA pool representing the 3'-ends of a population of mRNAs.

II. Applications of the Method for Display of mRNA Patterns

The method described above for the detection of patterns of mRNA expression in a tissue and the resolving of these patterns by gel electrophoresis has a number of applications. One of these applications is its use for the detection of a change in the pattern of mRNA expression in a tissue associated with a physiological or pathological change. In general, this method comprises:

(1) obtaining a first sample of a tissue that is not subject to the physiological or pathological change;

(2) determining the pattern of mRNA expression in the first sample of the tissue by performing the method of simultaneous sequence-specific identification of mRNAs corresponding to members of an antisense cRNA pool representing the 3'-ends of a population of mRNAs as described above to generate a first display of bands representing the 3'-ends of mRNAs present in the first sample;

(3) obtaining a second sample of the tissue that has been subject to the physiological or pathological change;

(4) determining the pattern of mRNA expression in the second sample of the tissue by performing the method of simultaneous sequence-specific identification of mRNAs corresponding to members of an antisense cRNA pool representing the 3'-ends of a population of mRNAs as described above to generate a second display of bands representing the 3'-ends of mRNAs present in the second sample; and (5) comparing the first and second displays to determine the effect of the physiological or pathological change on the pattern of mRNA expression in the tissue.

Typically, the comparison is made in adjacent lanes of a single gel.

Typically, a database comprising the data produced by the quantitation of the display of sequence-specific products is constructed and maintained using suitable computer hardware and computer software. Preferably, such a database further comprises data concerning sequence relationships, gene mapping, cellular distributions, and any other information considered relevant to gene function.

The tissue can be derived from the central nervous system. In particular, it can be derived from a structure within the central nervous system that is the retina, cerebral cortex, olfactory bulb, thalamus, hypothalamus, anterior pituitary, posterior pituitary, hippocampus, nucleus accumbens, amygdala, striatum, cerebellum, brain stem, suprachiasmatic nucleus, or spinal cord. When the tissue is derived from the central nervous system, the physiological or pathological change can be any of Alzheimer's disease, parkinsonism, ischemia, alcohol addiction, drug addiction, schizophrenia, amyotrophic lateral sclerosis, multiple sclerosis, depression, and bipolar manic-depressive disorder. Alternatively, the method of the present invention can be used to study circadian variation, aging, or long-term potentiation, the latter affecting the hippocampus. Additionally, particularly with reference to mRNA species occurring in particular structures within the central nervous system, the method can be used to study brain regions that are known to be involved in complex behaviors, such as learning and memory, emotion, drug addiction, glutamate neurotoxicity, feeding behavior, olfaction, viral infection, vision, and movement disorders.

This method can also be used to study the results of the administration of drugs and/or toxins to an individual by comparing the mRNA pattern of a tissue before and after the administration of the drug or toxin. Results of electroshock therapy can also be studied.

Alternatively, the tissue can be from an organ or organ system that includes the cardiovascular system, the pulmonary system, the digestive system, the peripheral nervous system, the liver, the kidney, skeletal muscle, and the reproductive system, or from any other organ or organ system of the body. For example, mRNA patterns can be studied from liver, heart, kidney, or skeletal muscle. Additionally, for any tissue, samples can be taken at various times so as to discover a circadian effect of mRNA expression. Thus, this method can ascribe particular mRNA species to involvement in particular patterns of function or malfunction.

The antisense cRNA pool representing the 3'-ends of mRNAs can be generated by steps (1)–(4) of the method as described above in Section I.

Similarly, the mRNA resolution method of the present invention can be used as part of a method of screening for a side effect of a drug. In general, such a method comprises:

(1) obtaining a first sample of tissue from an organism treated with a compound of known physiological function;

(2) determining the pattern of mRNA expression in the first sample of the tissue by performing the method of simultaneous sequence-specific identification of mRNAs corresponding to members of an antisense cRNA pool representing the 3'-ends of a population of mRNAs, as described above, to generate a first display of bands representing the 3'-ends of mRNAs present in the first sample;

(3) obtaining a second sample of tissue from an organism treated with a drug to be screened for a side effect;

(4) determining the pattern of mRNA expression in the second sample of the tissue by performing the method of simultaneous sequence-specific identification of mRNAs corresponding to members of an antisense cRNA pool representing the 3'-ends of a population of mRNAs, as described above, to generate a second display of bands representing the 3'-ends of mRNAs present in the second sample; and (5) comparing the first and second displays in order to detect the presence of mRNA species whose expression is not affected by the known compound but is affected by the drug to be screened, thereby indicating a difference in action of the drug to be screened and the known compound and thus a side effect.

In particular, this method can be used for drugs affecting the central nervous system, such as antidepressants, neuroleptics, tranquilizers, anticonvulsants, monoamine oxidase inhibitors, and stimulants. However, this method can in fact be used for any drug that may affect mRNA expression in a particular tissue. For example, the effect on mRNA expression of anti-parkinsonism agents, skeletal muscle relaxants, analgesics, local anesthetics, cholinergics, antispasmodics, steroids, non-steroidal anti-inflammatory drugs, antiviral agents, or any other drug capable of affecting mRNA expression can be studied, and the effect determined in a particular tissue or structure.

A further application of the method of the present invention is in obtaining the sequence of the 3'-ends of mRNA species that are displayed. In general, a method of obtaining the sequence comprises:

(1) eluting at least one cDNA corresponding to a mRNA from an electropherogram in which bands representing the 3'-ends of mRNAs present in the sample are displayed;

(2) amplifying the eluted cDNA in a polymerase chain reaction;

(3) cloning the amplified cDNA into a plasmid;

(4) producing DNA corresponding to the cloned DNA from the plasmid; and (5) sequencing the cloned cDNA.

The cDNA that has been excised can be amplified with the primers previously used in the PCR step. The cDNA can then be cloned into pCR II (Invitrogen, San Diego, Calif.) by TA cloning and ligation into the vector. Minipreps of the DNA can then be produced by standard techniques from subclones and a portion denatured and split into two aliquots for automated sequencing by the dideoxy chain termination method of Sanger. A commercially available sequencer can be used, such as a ABI sequencer, for automated sequencing. This will allow the determination of complementary sequences for most cDNAs studied, in the length range of 50–500 bp, across the entire length of the fragment.

These partial sequences can then be used to scan genomic data bases such as GenBank to recognize sequence identities and similarities using programs such as BLASTN and BLASTX. Because this method generates sequences from only the 3'-ends of mRNAs it is expected that open reading frames (ORFs) would be encountered only occasionally, as the 3'-untranslated regions of brain mRNAs are on average longer than 1300 nucleotides (J. G. Sutcliffe, supra). Potential ORFs can be examined for signature protein motifs.

The cDNA sequences obtained can then be used to design primer pairs for semiquantitative PCR to confirm tissue expression patterns. Selected products can also be used to isolate full-length cDNA clones for further analysis. Primer pairs can be used for SSCP-PCR (single strand conformation polymorphism-PCR) amplification of genomic DNA. For example, such amplification can be carried out from a panel of interspecific backcross mice to determine linkage of each PCR product to markers already linked. This can result in the mapping of new genes and can serve as a resource for identifying candidates for mapped mouse mutant loci and homologous human disease genes. SSCP-PCR uses synthetic oligonucleotide primers that amplify, via PCR, a small (100–200 bp) segment. (M. Orita et al., "Detection of Polymorphisms of Human DNA by Gel Electrophoresis as Single-Strand Conformation Polymorphisms," *Proc. Natl. Acad. Sci. USA* 86: 2766–2770 (1989); M. Orita et al., "Rapid and Sensitive Detection of Point Mutations in DNA Polymorphisms Using the Polymerase Chain Reaction," *Genomics* 5: 874–879 (1989)).

The excised fragments of cDNA can be radiolabeled by techniques well-known in the art for use in probing a northern blot or for in situ hybridization to verify mRNA distribution and to learn the size and prevalence of the corresponding full-length mRNA. The probe can also be used to screen a cDNA library to isolate clones for more reliable and complete sequence determination. The labeled probes can also be used for any other purpose, such as studying in vitro expression.

III. Panels and Degenerate Mixes of Primers

Another aspect of the present invention is panels of primers and degenerate mixtures of primers suitable for the practice of the present invention. These include:

(1) a panel of 5'-RT primers comprising 16 primers of the sequence A-G-G-T-C-G-A-C-G-G-T-A-T-C-G-G-N-N (SEQ ID NO: 3), wherein N is one of the four deoxyribonucleotides A, C, G, or T;

(2) a panel of 5'-PCR primers comprising 64 primers of the sequences A-G-G-T-C-G-A-C-G-G-T-A-T-C-G-G-N-N-N (SEQ ID NO: 5), wherein N is one of the four deoxyribonucleotides A, C, G, or T;

(3) a panel of 5'-PCR primers comprising 256 primers of the sequences A-G-G-T-C-G-A-C-G-G-T-A-T-C-G-G-N-N-N-N (SEQ ID NO: 6), wherein N is one of the four deoxyribonucleotides A, C, G, or T; and (4) a panel of 5'-PCR primers comprising 1024 primers of the sequences A-G-G-T-C-G-A-C-G-G-T-A-T-C-G-G-N-N-N-N-N (SEQ ID NO: 24), wherein N is one of the four deoxyribonucleotides A, C, G, or T; and (5) a panel of 5'-PCR primers comprising 4096 primers of the sequences A-G-G-T-C-G-A-C-G-G-T-A-T-C-G-G-N-N-N-N-N-N (SEQ ID NO: 25), wherein N is one of the four deoxyribonucleotides A, C, G, or T; and (6) a panel of anchor primers comprising 12 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-T-V-N (SEQ ID NO: 2), wherein V is a deoxyribonucleotide selected from the group consisting of A, C, and G; and N is a deoxyribonucleotide selected from the group consisting of A, C, G, and T;

(7) a panel of anchor primers comprising 3 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-T-V (SEQ ID NO: 23), wherein V is a deoxyribonucleotide selected from the group consisting of A, C, and G;

(8) a panel of 5'-RT primers comprising 4 different oligonucleotides each having the sequence G-G-T-C-G-A-C-G-G-T-A-T-C-G-G-N (SEQ ID NO: 9), wherein N is one of the four deoxyribonucleotides A, C, G, or T;

(9) a panel of 5'-RT primers comprising 16 different oligonucleotides each having the sequence G-T-C-G-A-C-G-G-T-A-T-C-G-G-N-N (SEQ ID NO: 7), wherein N is one of the four deoxyribonucleotides A, C, G, or T;

(10) a panel of 5'-PCR primers comprising 64 different oligonucleotides each having the sequence T-C-G-A-C-G-G-T-A-T-C-G-G-N-N-N (SEQ ID NO: 13), wherein N is one of the four deoxyribonucleotides A, C, G or T;

(11) a panel of 5'-PCR primers comprising 256 different oligonucleotides each having the sequence C-G-A-C-G-G-T-A-T-C-G-G-N-N-N-N (SEQ ID NO: 14), wherein N is one of the four deoxyribonucleotides A, C, G, or T;

(12) a panel of 5'-PCR primers comprising 1024 different oligonucleotides each having the sequence G-A-C-G-G-T-A-T-C-G-G-N-N-N-N-N (SEQ ID NO: 15), wherein N is one of the four deoxyribonucleotides A, C, G, or T;

(13) a panel of 5'-PCR primers comprising 4096 different oligonucleotides each having the sequence A-C-G-G-T-A-T-C-G-G-N-N-N-N-N-N (SEQ ID NO: 16), wherein N is one of the four deoxyribonucleotides A, C, G, or T;

(14) a panel of 5'-RT primers comprising 4 different oligonucleotides each having the sequence C-T-T-C-A-G-T-C-A-G-G-C-T-A-A-T-C-G-G-N (SEQ ID NO: 10), wherein N is one of the four deoxyribonucleotides A, C, G, or T;

(15) a panel of 5'-RT primers comprising 16 different oligonucleotides each having the sequence T-T-C-A-G-T-C-A-G-G-C-T-A-A-T-C-G-G-N-N (SEQ ID NO: 11), wherein N is one of the four deoxyribonucleotides A, C, G, or T;

(16) a panel of 5'-PCR primers comprising 64 different oligonucleotides each having the sequence T-C-A-G-T-C-A-G-G-C-T-A-A-T-C-G-G-N-N-N (SEQ ID NO: 12), wherein N is one of the four deoxyribonucleotides A, C, G, or T;

(17) a panel of 5'-PCR primers comprising 256 different oligonucleotides each having the sequence C-A-G-T-C-A-G-G-C-T-A-A-T-C-G-G-N-N-N-N (SEQ ID NO: 17), wherein N is one of the four deoxyribonucleotides A, C, G, or T;

(18) a panel of 5'-PCR primers comprising 1024 different oligonucleotides each having the sequence A-G-T-C-A-G-G-C-T-A-A-T-C-G-G-N-N-N-N-N (SEQ ID NO: 26), wherein N is one of the four deoxyribonucleotides A, C, G, or T;

(19) a panel of 5'-PCR primers comprising 4096 different oligonucleotides each having the sequence G-T-C-A-G-G-C-T-A-A-T-C-G-G-N-N-N-N-N-N (SEQ ID NO: 27), wherein N is one of the four deoxyribonucleotides A, C, G, or T;

(20) a degenerate mixture of anchor primers comprising a mixture of 3 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-T-V (SEQ ID NO: 23), wherein V is a deoxyribonucleotide selected from the group consisting of A, C, and G, each of the 3 primers being present in about an equimolar quantity; and

(21) a degenerate mixture of anchor primers comprising a mixture of 12 primers of the sequences A-A-C-T-G-G-A-A-G-A-A-T-T-C-G-C-G-G-C-C-G-C-A-G-G-A-A-T-T-T-T-T-T-T-T-T-T-T-T-T-T-T-T-T-V-N (SEQ ID NO: 2), wherein V is a deoxyribonucleotide selected from the group consisting of A, C, and G; and N is a deoxyribonucleotide selected from the group consisting of A, C, G, and T, each of the 12 primers being present in about an equimolar quantity.

The invention is illustrated by the following Example. The Example is for illustrative purposes only and is not intended to limit the invention.

EXAMPLE

Resolution of Brain mRNAs Using Primers Corresponding to Sequences of Known Brain mRNAs of Different Concentrations To demonstrate the effectiveness of the method of the present invention, it was applied using 5'-RT primers extended at their 3'-ends by two nucleotides and corresponding to the sequence of known brain mRNAs of different concentrations, such as neuron-specific enolase (NSE) at roughly 0.5% concentration (S. Forss-Petter et al., "Neuron-Specific Enolase: Complete Structure of Rat mRNA, Multiple Transcriptional Start Sites and Evidence for Translational Control," *J. Neurosci. Res.* 16: 141–156 (1986)), RC3 at about 0.01%, and somatostatin at 0.001% (G. H. Travis & J. G. Sutcliffe, "Phenol Emulsion-Enhanced DNA-Driven Subtractive cDNA Cloning: Isolation of Low-Abundance Monkey Cortex-Specific mRNAs," *Proc. Natl. Acad. Sci. USA* 85: 1696–1700 (1988)) to compare cDNAs made from libraries constructed from cerebral cortex, striatum, cerebellum and liver RNAs made as described above. On short autoradiographic exposures from any particular RNA sample, 50–100 bands were obtained. Bands were absolutely reproducible in duplicate samples. Approximately two-thirds of the bands differed between brain and liver samples, including the bands of the correct lengths corresponding to the known brain-specific mRNAs. This was confirmed by excision of the bands from the gels, amplification and sequencing. Only a few bands differed among samples for various brain regions for any particular 5'-RT primer, although some band intensities differed.

The band corresponding to NSE, a relatively prevalent mRNA species, appeared in all of the brain samples but not in the liver samples, but was not observed when any of the last three single nucleotides within the four-base 3'-terminal sequence -N-N-N-N was changed in the synthetic 5'-primer. When the first N was changed, a small amount of bleedthrough is detected. For the known species, the intensity of the autoradiographic signal was roughly proportional to mRNA prevalence, and mRNAs with concentrations of one part in $10^5$ or greater of the poly(A)$^+$ RNA were routinely visible, with the occasional problem that cDNAs that migrated close to more intense bands were obscured.

Figure 2:
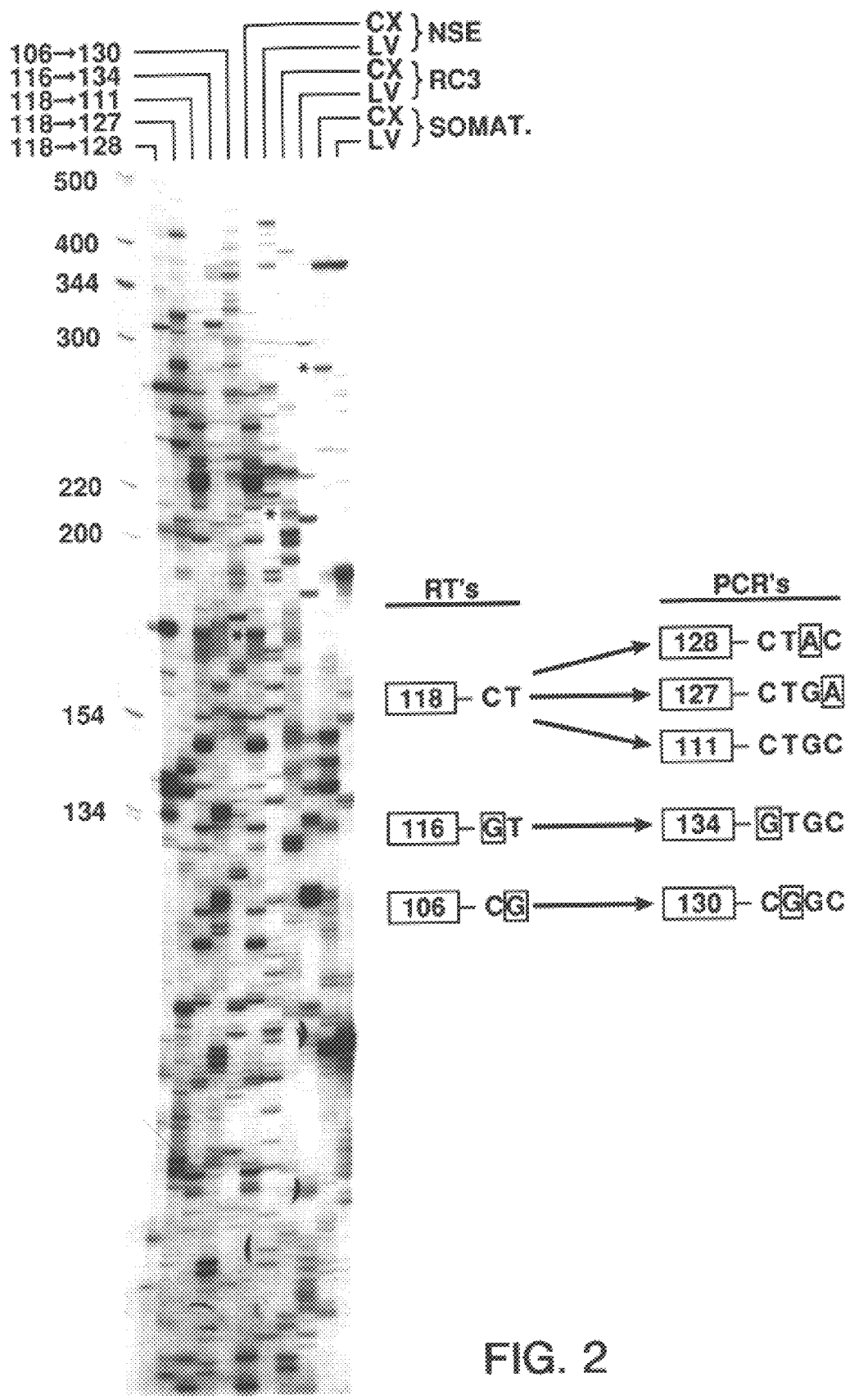
FIG. 2 is an autoradiogram of a gel showing the result of performing the method of the present invention using several 5'-primers in the PCR step corresponding to known sequences of brain mRNAs and using liver and brain mRNA as starting material.

A sample of the data is shown in FIG. 2. In the 5 gel lanes on the left, cortex cRNA was substrate for reverse transcription with the 5'-RT primer A-G-G-T-C-G-A-C-G-G-T-A-T-C-G-G-N-N (SEQ ID NO: 3) where -N-N is -C-T (primer 118), -G-T (primer 116) or -C-G (primer 106). The PCR amplification used 5'-PCR primers A-G-G-T-C-G-A-C-G-G-T-A-T-C-G-G-N-N-N-N (SEQ ID NO: 6) where -N-N-N-N is -C-T-A-C (primer 128), -C-T-G-A (primer 127), -C-T-G-C (primer 111), -G-T-G-C (primer 134), and -C-G-G-C (primer 130), as indicated in FIG. 2. Primers 118 and 111 match the sequence of the two and four nucleotides, respectively, downstream from the MspI site located the nearest the 3'-end of the NSE mRNA sequence. Primer 127 is mismatched with the NSE sequence in the last (−1) position, primer 128 in the next-to-last (−2) position, primers 106 and 130 in the −3 position, and primers 116 and 134 in the −4 position. Primer 134 extended two nucleotides further upstream than the others shown here, hence its PCR products are two nucleotides longer relative to the products in other lanes.

In each lane, 50–100 bands were visible in 15-minute exposures using $^{32}$P-dCTP to radiolabel the products. These bands were apparently distinct for each primer pair, with the exception that a subset of the 118–111 bands appeared more faintly in the 116–134 lane, trailing by two nucleotides, indicating bleedthrough in the four position.

The 118–111 primer set was used again on separate cortex (CX) and liver (LV) cRNAs. The cortex pattern was identical to that in lane 118–111, demonstrating reproducibility. The liver pattern differed from CX in the majority of species. The asterisk indicates the position of the NSE product. Analogous primer sets detected RC3 and somatostatin (somat) products (asterisks) in CX but not LV lanes. The relative band intensities of a given PCR product can be compared within lanes using the same primer set, but not different sets.

This example demonstrates the feasibility and reproducibility of the method of the present invention and its ability to resolve different mRNAs. It further demonstrates that prevalence of particular mRNA species can be estimated from the intensity of the autoradiographic signal. The assay allows mRNAs present in both high and low prevalence to be detected simultaneously.

ADVANTAGES OF THE PRESENT INVENTION

The present method can be used to identify genes whose expression is altered during neuronal development, in models of plasticity and regeneration, in response to chemical or electrophysiological challenges such as neurotoxicity and long-term potentiation, and in response to behavioral, viral, drug/alcohol paradigms, the occurrence of cell death or apoptosis, aging, pathological conditions, and other conditions affecting mRNA expression. Although the method is particularly useful for studying gene expression in the nervous system, it is not limited to the nervous system and can be used to study mRNA expression in any tissue. The method allows the visualization of nearly every mRNA expressed by a tissue as a distinct band on a gel whose intensity corresponds roughly to the concentration of the mRNA.

The method has the advantage that it does not depend on potentially irreproducible mismatched random priming, so that it provides a high degree of accuracy and reproducibility. Moreover, it reduces the complications and imprecision generated by the presence of concurrent bands of different length resulting from the same mRNA species as the result of different priming events. In methods using random priming, such concurrent bands can occur and are more likely to occur for mRNA species of high prevalence. In the present method, such concurrent bands are avoided.

The method provides sequence-specific information about the mRNA species and can be used to generate primers, probes, and other specific sequences.

Although the present invention has been described in considerable detail, with reference to certain preferred versions thereof, other versions are possible. Therefore, the spirit and scope of the appended claims should not be limited to the description of the preferred versions contained herein.

We claim:

1. A method for recognizing sequence identities and similarities between the sequence of 3'-ends of mRNA molecules present in a sample and a database of sequences, comprising the steps of:

(a) preparing a double-stranded cDNA population from an mRNA population using a mixture of anchor primers, the anchor primers each including: (i) a tract of from 7 to 40 T residues; (ii) a site for cleavage by a first restriction endonuclease that recognizes more than six bases, the site for cleavage being located to the 5'-side of the tract of T residues; (iii) a first stuffer segment of from 4 to 40 nucleotides, the first stuffer segment being located to the 5'-side of the site for cleavage by the first restriction endonuclease; and (iv) phasing residues located at the 3' end of each of the anchor primers selected from the group consisting of -V and -V-N, wherein V is a deoxyribonucleotide selected from the group consisting of A, C, and G; and N is a deoxyribonucleotide selected from the group consisting of A, C, G, and T, the mixture including anchor primers containing all possibilities for V and N where the phasing residues in the mixture are defined by one of -V or -V-N;

(b) cleaving the double-stranded cDNA population with the first restriction endonuclease and with a second restriction endonuclease, the second restriction endonuclease recognizing a four-nucleotide sequence, to form a population of double-stranded cDNA molecules having first and second termini, respectively;

(c) inserting the double-stranded cDNA molecules from step (b) each into a vector in an orientation that is antisense with respect to a bacteriophage-specific promoter within the vector to form a population of vectors containing the inserted cDNA molecules, said inserting defining 3' and 5' flanking vector sequences such that 5' is upstream from the sense strand of the inserted cDNA and 3' is downstream of the sense strand, and said vector having a 3' flanking nucleotide sequence of from at least 15 nucleotides in length between said first restriction endonuclease site and a site defining transcription initiation in said promoter;

(d) generating linearized fragments containing the inserted cDNA molecules by digestion of the vectors produced in step (c) with at least one restriction endonuclease that does not recognize sequences in the inserted cDNA molecules or in the bacteriophage-specific promoter, but does recognize sequences in the vector such that the resulting linearized fragments have a 5' flanking vector sequence of at least 15 nucleotides 5' to the site of insertion of the cDNA sample into the vector at the cDNA's second terminus;

(e) generating a cRNA preparation of antisense cRNA transcripts by incubation of the linearized fragments with a bacteriophage-specific RNA polymerase capable of initiating transcription from the bacteriophage-specific promoter;

(f) dividing the cRNA preparation into subpools and transcribing first-strand cDNA from each subpool, using a reverse transcriptase and a 5'-RT primer in each subpool, each one of the 5'-RT primers defined as having a 3'-terminus consisting of -N$_x$, wherein "N" is one of the four deoxyribonucleotides A, C, G, or T, and "x" is an integer from 1 to 5, the 5'-RT primer being 15 to 30 nucleotides in length and complementary to the 5' flanking vector sequence with the primer's complementarity extending across into the insert-specific nucleotides of the cRNA in a number of nucleotides equal to "x", wherein a different one of said 5'-RT primers is used in different subpools and wherein there are 4 subpools if "x"=1, 16 subpools if "x"=2, 64 subpools if "x"=3,256 subpools if "x"=4, and 1,024 subpools if "x"=5;

(g) using the product of first-strand cDNA transcription in each of the subpools as a template for a polymerase chain reaction with a 3'-PCR primer of 15 to 30 nucleotides in length that is complementary to 3' flanking vector sequences between said first restriction endonuclease site and the site defining transcription initiation by the bacteriophage-specific promoter and a 5'-PCR primer having a 3'-terminus consisting of N$_x$-N$_y$, where "N" and "x" are as in step (f) -N$_x$ is the same sequence as in the 5'-RT primer from which first-strand cDNA was made for that subpool, and "y" is a whole integer such that x+y equals an integer selected from the group consisting of 3, 4, 5 and 6, the 5'-PCR primer being 15 to 30 nucleotides in length and complementary to the 5' flanking vector sequence with the 5'-PCR primer's complementarity extending across into the insert-specific nucleotides of the cRNA in a number of nucleotides equal to "x+y", to produce polymerase chain reaction amplified fragments;

(h) resolving the polymerase chain reaction amplified fragments to generate a display of sequence-specific products representing the 3'-ends of different mRNAs present in the mRNA population;

(i) eluting at least one of the sequence-specific products;

(1) amplifying the eluted sequence-specific products in a polymerase chain reaction to produce amplified cDNA;

(k) cloning the amplified cDNA into a plasmid;

(l) producing DNA corresponding to the cloned DNA from the plasmid;

(m) determining the sequence of the cloned DNA;

(n) determining corresponding nucleotide sequences from a database of nucleotide sequences, said corresponding nucleotide sequences being delimited by the distal recognition site for the second endonuclease and the beginning of the poly(A) tail; and (o) comparing the sequence of the cloned cDNA to the corresponding nucleotide sequences, thereby recognizing sequence identities and similarities between the sequence of 3'-ends of mRNA molecules present in a sample and a database of sequences.

2. The method of claim 1 wherein the phasing residues in step (a) are -V-N.

3. The method of claim 1 wherein the phasing residues in step (a) are -V.

4. The method of claim 1 wherein the "x" in step (f) is 2.

5. The method of claim 1 wherein the "x" in step (f) is 1.

6. The method of claim 5 wherein the "y" in step (g) is 3.

7. The method of claim 5 wherein the "y" in step (g) is 4.

8. The method of claim 1 wherein the phasing residues in step (a) are -V-N, the "x" in step (f) is 2, and the "y" in step (g) is 2.

9. The method of claim 1 wherein the phasing residues in step (a) are -V-N, the "x" in step (f) is 1, and the "y" in step (g) is 3.

10. The method of claim 1 wherein the phasing residues in step (a) are -V-N, the "x" in step (f) is 1, and the "y" in step (g) is 4.

11. The method of claim 1 wherein the phasing residues in step (a) are -V, the "x" in step (f) is 1, and the "y" in step (g) is 3.

12. The method of claim 1 wherein the phasing residues in step (a) are -V, the "x" in step (f) is 1, and the "y" in step (g) is 4.

13. The method of claim 1 wherein the anchor primers each have 18 T residues in the tract of T residues.

14. The method of claim 1 further comprising the step of (p) comparing the length and amount of the sequence-specific products in a two dimensional graphical display.

15. The method of claim 14 further comprising the steps of (q) determining the expected length of the corresponding nucleotide sequence, which is equal to the sum of the lengths of the corresponding nucleotide sequence determined from the database, the length of the 5'PCR sequence hybridizable to vector sequence, the length of the remaining anchor primer sequence, an intervening segment of vector sequence and the length of the 3'PCR sequence hybridizable to vector sequence; and (r) comparing the length of the PCR product to the determined expected length of the corresponding nucleotide sequence, wherein the expected length of corresponding nucleotide sequence is indicated in the two dimensional graphical display by the use of a graphical symbol or text character.

16. The method of claim 1 wherein a second stuffer segment is interposed between the site for cleavage by a restriction endonuclease that recognizes more than six bases and the tract of T residues.

17. The method of claim 1 wherein the anchor primers have the sequence A-A-C-T-G-G-A-A-G-A-A-T-T-C-G-C-G-G-C-C-G-C-A-G-G-A-A-T-T-T-T-T-T-T-T-T-T-T-T-T-T-T-T-T-T-V-N (SEQ ID NO: 2).

18. The method of claim 1 wherein the anchor primers have the sequence A-A-C-T-G-G-A-A-G-A-A-T-T-C-G-C-G-G-C-C-G-C-A-G-G-A-A-T-T-T-T-T-T-T-T-T-T-T-T-T-T-T-T-T-T-V (SEQ ID NO: 23).

19. The method of claim 1 wherein the bacteriophage-specific promoter is selected from the group consisting of T3 promoter, T7 promoter and SP6 promoter.

20. The method of claim 16 wherein the bacteriophage-specific promoter is T3 promoter.

21. The method of claim 1 wherein the 5'-RT primers for priming of transcription of cDNA from cRNA have the sequence A-G-G-T-C-G-A-C-G-G-T-A-T-C-G-G-N-N (SEQ ID NO: 3).

22. The method of claim 1 wherein the 5'-RT primers for priming of transcription of cDNA from cRNA have the sequence G-T-C-G-A-C-G-G-T-A-T-C-G-G-N-N (SEQ ID NO: 7).

23. The method of claim 1 wherein the vector is the plasmid pBC SK+ cleaved with ClaI and NotI and the 3'-PCR primer in step (g) is G-A-A-C-A-A-A-A-G-C-T-G-G-A-G-C-T-C-C-A-C-C-G-C (SEQ ID NO: 4).

24. The method of claim 1 wherein the vector is the plasmid pBC SK+ cleaved with ClaI and NotI and the 3'-PCR primer in step (g) is A-A-G-C-T-G-G-A-G-C-T-C-C-A-C-C (SEQ ID NO: 8).

25. The method of claim 1 wherein the second restriction endonuclease recognizing a four-nucleotide sequence is MspI.

26. The method of claim 1 wherein the second restriction endonuclease recognizing a four-nucleotide sequence is selected from the group consisting of MboI, DpnII, Sau3AI, Tsp509I, HpaII, BfaI, Csp6I, MseI, HhaI, NlaIII, TaqI, MspI, MaeII and HinP1I.

27. The method of claim 1 wherein the first restriction endonuclease that recognizes more than six bases is selected from the group consisting of AscI, BaeI, FseI, NotI, PacI, PmeI, PpuMI, RsrII, SapI, SexAI, SfiI, SgfI, SgrAI, SrfI, Sse8387I and SwaI.

28. The method of claim 1 wherein the first restriction endonuclease that recognizes more than six bases is NotI.

29. The method of claim 1 wherein the restriction endonuclease used in step (d) has a nucleotide sequence recognition that includes the four-nucleotide sequence of the second restriction endonuclease used in step (b).

30. The method of claim 29 wherein the second restriction endonuclease is MspI and the restriction endonuclease used in step (d) is Sma I.

31. The method of claim 29 wherein the second restriction endonuclease is TaqI and the restriction endonuclease used in step (d) is XhoI.

32. The method of claim 29 wherein the second restriction endonuclease is HinP1I and the restriction endonuclease used in step (d) is NarI.

33. The method of claim 29 wherein the second restriction endonuclease is MaeII and the restriction endonuclease used in step (d) is AatII.

34. The method of claim 1 wherein the vector of step (c) is in the form of a circular DNA molecule having first and second vector restriction endonuclease sites flanking a vector stuffer sequence, and further comprising the step of digesting the vector with restriction endonucleases that cleave the vector at the first and second vector restriction endonuclease sites.

35. The method of claim 34 wherein the vector stuffer sequence includes an internal vector stuffer restriction endonuclease site between the first and second vector restriction endonuclease sites.

36. The method of claim 35 wherein the step (d) includes digestion of the vector with a restriction endonuclease which cleaves the vector at the internal vector stuffer restriction endonuclease site.

37. The method of claim 36 wherein the restriction endonuclease used in step (d) also cleaves the vector at the internal vector stuffer restriction endonuclease site.

* * * * *